US011590084B2

(12) United States Patent
Bielski et al.

(10) Patent No.: US 11,590,084 B2
(45) Date of Patent: Feb. 28, 2023

(54) MICROCAPSULES FOR CONTROLLED DELIVERY OF AN ACTIVE PHARMACEUTICAL INGREDIENT

(71) Applicants: Roman Bielski, Coopersburg, PA (US); Zbigniew Janusz Witczak, Mountain Top, PA (US)

(72) Inventors: Roman Bielski, Coopersburg, PA (US); Zbigniew Janusz Witczak, Mountain Top, PA (US)

(*) Notice: Subject to any disclaimer, the term of this patent is extended or adjusted under 35 U.S.C. 154(b) by 0 days.

(21) Appl. No.: 16/178,324

(22) PCT Filed: Apr. 28, 2017

(86) PCT No.: PCT/US2017/030268
§ 371 (c)(1),
(2) Date: Nov. 1, 2018

(87) PCT Pub. No.: WO2017/192407
PCT Pub. Date: Nov. 9, 2017

(65) Prior Publication Data
US 2019/0125687 A1 May 2, 2019

Related U.S. Application Data

(60) Provisional application No. 62/330,793, filed on May 2, 2016.

(51) Int. Cl.
| C05G 3/00 | (2020.01) |
| A61K 9/50 | (2006.01) |
| A61Q 19/00 | (2006.01) |
| A61K 8/11 | (2006.01) |
| B01J 13/16 | (2006.01) |
| A61K 31/565 | (2006.01) |

(52) U.S. Cl.
CPC ............ *A61K 9/5026* (2013.01); *A61K 8/11* (2013.01); *A61K 9/5031* (2013.01); *A61K 31/565* (2013.01); *A61Q 19/00* (2013.01); *B01J 13/16* (2013.01); *C05G 3/00* (2013.01); *A61K 2800/10* (2013.01); *A61K 2800/412* (2013.01)

(58) Field of Classification Search
None
See application file for complete search history.

(56) References Cited

U.S. PATENT DOCUMENTS

| 4,251,387 A | 2/1981 | Lim et al. |
| 4,666,641 A | 5/1987 | Fickat et al. |
| 4,741,872 A | 5/1988 | DeLuca et al. |
| 4,931,362 A | 6/1990 | Zsifkovitz et al. |
| 5,487,390 A * | 1/1996 | Cohen ............... A61K 9/1271 424/501 |
| 5,622,656 A | 4/1997 | Huc et al. |
| 5,779,944 A | 7/1998 | Kopolow |
| 6,359,031 B1 | 3/2002 | Lykke et al. |
| 6,379,703 B1 | 4/2002 | Lyon et al. |
| 6,828,025 B2 | 12/2004 | Ali et al. |
| 6,849,271 B2 | 2/2005 | Vaghefi et al. |
| 6,861,064 B1 | 3/2005 | Laakso et al. |
| 8,747,999 B2 | 6/2014 | Grey et al. |
| 2002/0136773 A1* | 9/2002 | Scher ............... A01N 25/28 424/497 |
| 2005/0271735 A1* | 12/2005 | Stover ............... A01N 25/28 424/490 |
| 2011/0008427 A1 | 1/2011 | Biggs et al. |
| 2011/0200654 A1* | 8/2011 | Habar ............... B01J 13/18 424/401 |
| 2014/0186630 A1 | 7/2014 | Schwantes |
| 2015/0231589 A1 | 8/2015 | Arumugam et al. |
| 2017/0002301 A1* | 1/2017 | Dihora ............... A61K 8/31 |
| 2017/0113200 A1 | 4/2017 | Zhang et al. |

FOREIGN PATENT DOCUMENTS

| WO | 94/023832 | 10/1994 |
| WO | 94/23832 | 10/1994 |
| WO | 00/59616 | 10/2000 |
| WO | 01/019509 | 3/2001 |
| WO | 01/019509 A1 | 3/2001 |
| WO | 2006/096051 | 9/2006 |
| WO | 2006/096051 A1 | 9/2006 |
| WO | WO-2015165834 A1 * | 11/2015 ............ A01N 25/28 |

(Continued)

OTHER PUBLICATIONS

Dispinar et al., Polym. Chem., 2013, vol. 4, pp. 763-772. (Year: 2013).*

(Continued)

*Primary Examiner* — Brian Gulledge
(74) *Attorney, Agent, or Firm* — Peter D. Mlynek; Law Offices of Peter D. Mlynek

(57) ABSTRACT

The present invention relates a microcapsule that comprises an active pharmaceutical ingredient and a polymeric shell comprised of polymeric materials such as polyether, polyester, polyamine, polyamide, polyurea, polyurethane, polythiocarbamate, and polythiocarbonate. The outer surface of shell comprises surface functional groups such as hydroxide, primary amine, carboxylic acid, or protected forms thereof. These surface functional groups may be reacted further with reactants to place specific organic groups on the surface of the microcapsule. Such microcapsules are prepared by a modified interfacial condensation polymerization.

20 Claims, 5 Drawing Sheets

(56) References Cited

FOREIGN PATENT DOCUMENTS

WO 2017/089115 6/2017
WO 2017/089115 A1 6/2017

OTHER PUBLICATIONS

S. Bhaskar et al., Towards Designer Microparticles: Simultaneous Control of Anisotropy, Shape, and Size, Small Journal, 2010, vol. 6, No. 3, pp. 404-411; DOI: 10.1002/smll.200901306; Wiley-VCH Verlag GmbH & Co. KGaA, Weinheim, Germany.

E. M. Sletten and C. R. Bertozzi, Bioorthogonal Chemistry: Fishing for Selectivity in a Sea of Functionality; Angew. Chem. Int. Ed. Engl., 2009, vol. 49, pp. 6974-6998; Wiley-VCH, Berlin, Germany.

D. C. Kennedy et al., Glycosylated Nanoscale Surfaces: Preparation and Applications in Medicine and Molecular Biology, Chem. Eur. J., 2013, vol. 19, pp. 3974-3800; Wiley-VCH, Berlin, Germany.

C. Tomaro-Duchesneau et al. Microencapsulation for the therapeutic delivery of drugs; J. Pharmaceutics 2013, vol. 2013, Art. ID 103527; Hindawi Publ. Corp., London, UK.

C. E. Mora-Huertas, Polymer-based Nanocapsules for Drug Delivery; Int'l. J. Pharmaceutics, 2010, vol. 385, pp. 113-142; Elsevier B.V., Amsterdam, Netherlands.

P. Kothamasu, et al., Nanocapsules: The Weapon for Novel Drug Delivery Systems; BioImpacts, 2012, vol. 2,iss. 2, pp. 71-81; Tabriz University of Medical Sciences, Tabriz, Iran.

A. Musyanovych and K. Landfester, Polymer Micro- and Nanocapsules as Biological Carriers with Multifunctional Properties, Macromol. Biosci. 2014, vol. 14, pp. 458-477; Wiley-VCH Verlag GmbH & Co., Weinheim, Germany.

U. Shimanovich et al., Protein Micro- and Nano-capsules for Biomedical Applications, Chem. Soc. Rev. 2013, DOI: 10.1039/c3cs60376h; The Royal Society of Chemistry, London, UK.

W. Liu et al., Preparation of Uniform-Sized Multiple Emulsions and Micro/Nano Particulates for Drug Delivery by Membrane Emulsification, J. Pharm. Sci., 2011, vol. 100, iss. 1, pp. 75-93; Wiley-Liss, Inc.

S. Bhaskar et al., Towards Designer Microparticles: Simultaneous Control of Anisotropy, Shape, and Size, Smail Journal, 2010, vol. 6, No. 3, pp. 404-411; DOI: 10.1002/smll.200901306; Wiiey-VCH Verlag GmbH & Co. KGaA, Weinheim, Germany.

H. Jahangirian et al., A Review of Drug Delivery Systems Based on Nanotechnology and Green Chemistry: Green Nanomedicine, Int. J. Nanomedicine, 2017, vol. 12, pp. 2957-2978; Dove Medical Press Limited, London, UK.

R. Bielski and Z. Witczak, Strategies for Coupling Molecular Units if Subsequent Decoupling is Required, Chem. Rev., 2013, vol. 113, pp. 2205-2243; American Chemical Society.

E. M. Sletten and C. R. Bertozzi, Bloorthogonal Chemistry: Fishing for Selectivity in a Sea of Functionality; Angew. Chem. Int. Ed. Engl., 2009, vol. 49, pp. 6374-6998; Wiley-VCH, Berlin, Germany.

M. Boyce, C. R. Bertozzi, Bringing chemistry to Life; Nat. Methods, 2011, vol. 8, p. 638-642: Nature Publishing Group, London, UK.

D. Lenses et al. Biodegradable polymeric microcapsules for selective ultrasound-triggered drug release; Soft Matter, 2011, vol. 7, pp. 5417-5422; Royal Soc. Chem., London, UK.

D. C. Kennedy et al., Glycosylated Nanoscale Surfaces: Preparation and Applications in Medicine and Molecular Biology, Chem. Eur. J., 2013, vol. 19, pp. 3974-3800; Wiiey-VCH, Berlin, Germany.

J. D. Roberts and M. C. Caserio, Basic Principles of Organic Chemistry, second edition, 1977, W. A. Benjamin, Inc., Menlo Park, CA. ISBN 0-8053-8329-8, section 13.10.

A. Streitwieser, Jr. and C. H. Heathcock, 1981, introduction to Organic Chemistry, second edition, MacMillan Publishing Co., Inc., New York., ISBN 0-02-418050-5, section 16.4.

T. W. Greene and P. G. M. Wuts, Protective Groups in Organic Synthesis, third edition, 1999, ISBN:9780471160199, DOI: 10.1002/0471220574.

The Organic Synthesis Archive, Protecting Group, https://synarchive.com/protecting~group; accessed Jan. 3, 2020.

S. Jyouthi Sri et al. Microencapsulation: A Review; Int J. Pharma Bio Sci. 2012, vol. 3, iss. 1, pp. 509-531; IJPBS, India.

S. Kalepu and V. Nekkanti, Insoluble Drug Delivery Strategies: Review of Recent Advances and Business Prospects; Acta Pharmaceutica Sinica B, 2015, vol. 5, iss. 5, pp. 442-453; Elsevier B. V., Netherlands.

C. Tomaro-Duchesneau et al. Microencapsulation for the therapeufic delivery of drugs; J. Pharmaceutics 2013, vol. 2013, Art. ID 103527; Hindawi Publ. Corp., London, UK.

\* cited by examiner

MICROCAPSULES FOR CONTROLLED DELIVERY OF AN ACTIVE PHARMACEUTICAL INGREDIENT

CROSS-REFERENCE TO RELATED APPLICATIONS

The present application is a 35 U.S.C. § 371(c) National Statege Application of International Patent Application No. PCT/US17/030268, with filing date of 28 Apr. 2017, which in turn claims priority under 35 U.S.C. § 119(a) to U.S. Provisional Patent Application No. 62/330,793, filed on 2 May 2016. Each of these applications are incorporated herein by reference in its entirety.

FIELD OF THE INVENTION

The present invention is directed to microcapsules for use in drug delivery.

DESCRIPTION OF RELATED TECHNOLOGY

Medically active substances are often introduced into the body in a microencapsulated form. Microencapsulation is usually performed to control the duration of the release of a drug into the blood or gastrointestinal system. One common aim of microencapsulation is to extend the duration that an active compound is released into a living system, resulting in extending the therapeutic activity of a drug long after a pill containing the drug is ingested or an intravenous administration of the drug is ceased.

A second valuable aim of microencapsulation is to prevent the premature release of the active compound. For example, a microcapsule shell can be unaffected by the low stomach pH which allows a drug to remain unchanged in microencapsulated form until it reaches farther along the gastrointestinal tract where the pH is higher.

Another purpose of microencapsulation is to prevent any contact between the active compound and the environments that the compound may encounter until the microcapsule reaches the desired location within the body, where the payload containing the active ingredient is released.

A review of microencapsulation is published in S. Jyothi Sri et al. *Int'l J. Pharma Bio Sci.* 2012, 3(1), 509-531. Microencapsulation is the process of surrounding or enveloping one substance within another substance on a very small scale, yielding capsules ranging from less than one micron to several hundred microns in size. The encapsulation efficiency of the microparticles or microsphere or microcapsule depends upon different factors like concentration of the polymer, solubility of polymer in solvent, rate of solvent removal, solubility of organic solvent in water etc. Microencapsulation may be achieved by a myriad of techniques. Substances may be microencapsulated with the intention that the core material be confined within capsule walls for a specific period of time. Alternatively, core materials may be encapsulated so that the core material will be released either gradually through the capsule walls, known as controlled release or diffusion, or when external conditions trigger the capsule walls to rupture, melt, or dissolve.

Microencapsulation is useful in delivering insoluble drugs. Sandeep Kalepu and Vijaykumar Nekkanti, *Acta Pharmaceutica Sinica B*, 2015, 5(5), 442-453, disclose that the emerging trends in the combinatorial chemistry and drug design have led to the development of drug candidates with greater lipophilicity, high molecular weight and poor water solubility. Majority of the failures in new drug development have been attributed to poor water solubility of the drug. About 40% of drugs with market approval and nearly 90% of molecules in the discovery pipeline are poorly water-soluble. There are tremendous difficulties scientists encounter when addressing the issue of solubility when drugs are not encapsulated.

Microencapsulation for the therapeutic delivery of drugs has been reviewed in C. Tomaro-Duchesneau et al. *J. Pharmaceutics* (Hindawi Pub. Corp.) 2013, Art. ID 103527. Microencapsulation is a technology that has shown significant promise in biotherapeutics, and other applications. It has been proven useful in the immobilization of drugs, live mammalian and bacterial cells and other cells, and other biopharmaceutics molecules, as it can provide material structuration, protection of the enclosed product, and controlled release of the encapsulated contents, all of which can ensure efficient and safe therapeutic effects.

The microcapsules of prior art have been prepared in any of several known methods, such as interfacial polymerization processes. Polymer-based nanocapsules for drug delivery were reviewed in C. E. Mora-Hueras, *Int'l J. Pharmaceutics*, 2010, 385, 113-142. There are various different preparation methods of microencapsulating active pharmaceutical ingredients: nanoprecipitation, emulsion-diffusion, double emulsification, emulsion-coacervation, polymer-coating and layer-by-layer encapsulation of the active substance.

Functionalized microcapsules for use in fabric treatment have been disclosed in U.S. Pat. No. 8,747,999. That patent disclosed microcapsules that have two different functional groups on the outer shell of the particles that allow deposition onto the textile surfaces and subsequent covalent bonding of the particles onto the textile. Such microcapsules are reactive towards the fiber.

Microcapsules have been used to deliver active pharmaceutical ingredients. For example, Patent Publication No. WO2006/000114 discloses a method for encapsulating a liquid, comprising the steps of providing a suspension of droplets of the liquid to be encapsulated; stabilizing the suspension of droplets with a surfactant; adding a layered inorganic material to the stabilized suspension; and subjecting the suspension to a treatment which establishes that a shell of a hybrid material is formed around the droplets, wherein the hybrid material comprises at least part of the inorganic material and at least part of the surfactant.

Another encapsulation method is disclosed in U.S. Pat. No. 6,861,064. The method of encapsulating an active substance in a biodegradable polymer comprises: dissolving said biodegradable polymer in an organic solvent; dispersing said active substance in the organic solution to provide a dispersion with the active substance as the inner phase thereof; or alternatively emulsifying said active substance, dissolved in water or other aqueous solvent therefor, in the organic solution to provide an emulsion with the active substance as the inner aqueous phase thereof; and subjecting the dispersion to an encapsulation operation with an aqueous polyethylene glycol solution as a continuous phase to provide micro- or nanoparticles having the active substance encapsulated therein. Such particles exhibit sustained release.

Microspheres, processes for the manufacture of said microspheres, pharmaceutical compositions comprising said microspheres, and sustained release methods of administering an effective pharmaceutical amount of a bioactive compound to a subject are disclosed in U.S. Pat. No. 6,849,271. The microspheres comprise a water-insoluble organic matrix comprising an interior region, throughout which are homogeneously dispersed a plurality of microcapsules consisting essentially of a core of bioactive compound coated with material containing charged organic groups and a surface region substantially free of said bioactive compound.

Microencapsulation of polar liquids in copolymer shells is taught in U.S. Pat. No. 6,828,025. To encapsulate polar core-oils an amphiphilic polymer is required that has low interfacial tensions with both the oil phase and the water phase. For example, Poly(methyl methacrylate-co-poly(ethylene glycol) methacrylate) (PMMA-co-PegMA) was prepared in suspension polymerization conditions using atom transfer radical polymerization (ATRP). ATRP ensures that the water-soluble comonomer, PegMA, is incorporated into every polymer chain throughout the polymerization reaction so that all chains possess the desired amphiphilic character. Crosslinking of PMMA-co-PegMA with diethylene glycol dimethacrylate (DegDMA) yielded hollow capsular particles at 31 mol % PegMA in the terpolymer.

Preparation of microparticles having a selected release profile is disclosed in U.S. Pat. No. 6,379,703. A method for preparing microparticles that exhibit controlled release of an effective amount of an active agent over an extended period is taught. More particularly, a method is provided for preparing microparticles having a selected release profile for release of active agent contained in the microparticles. By adjusting the degree of drying that is performed during the preparation of the microparticles, the release profile can be controlled. By performing no intermediate drying, an initial burst and a substantially linear release profile is achieved. By performing substantially complete intermediate drying, an initial lag phase and a substantially sigmoidal release profile is achieved.

Particles having a polymeric shell and their production are also disclosed in U.S. Pat. No. 6,359,031. Such particles have a hydrophilic core, for instance including an enzyme and a polymer, surrounded by a shell formed by interfacial condensation polymerization in the presence of a polymeric stabilizer. The polymeric stabilizer is a random copolymer that will concentrate at the interface between oil and water and association by ionic interaction, condensation or otherwise is achieved between the stabilizer and one of the reactants before reaction with the other reactant. Dispersions of aqueous capsules in an aqueous medium are also possible.

Biodegradable microcapsules based on serum albumin, the preparation thereof and the application thereof to the release of drugs in situ are taught in U.S. Pat. No. 4,666,641. A feature of those microcapsules is that their wall consists of serum albumin, a portion of which is crosslinked by interfacial polymerization with the aid of an acylating bifunctional reagent, and the other, non-crosslinked portion of which is denatured by means of an alcohol.

Water dispersible perfluoroether polymer encapsulates are taught in U.S. Pat. No. 5,779,944, wherein water insoluble encapsulate comprise a water insoluble polymer of a perfluoroether containing perfluorinated isopropyloxy units and having a number average molecular weight of between about 450 and about 15,000. The polymer is encapsulated in a water soluble, non-halogenated polymer and to the stable, homogeneous, aqueous compositions of the encapsulated perfluoroether polymer in various formulations of pharmaceutically active substances.

Process of manufacture of biodegradable microcapsules having walls composed of crosslinked atelocollagen and polyholosides is taught in U.S. Pat. No. 5,622,656. Microcapsules with a mixed wall of crosslinked atelocollagen and polyholosides, for example glycosaminoglycans, and to processes for the manufacture of the said microcapsules are disclosed. Those microcapsules comprise a mixed wall of crosslinked atelocollagen and polyholosides, for example glycosaminoglycans, the proportion of polyholosides, for example glycosaminoglycans, relative to the atelocollagen preferably being between 18 and 50% by weight. Such microcapsules can be manufactured either by a process involving interfacial crosslinking or by the extrusion of a laminar flow, which is broken up by vibrations into individual droplets, which fall into a crosslinking bath.

Particles prepared by trans-acylation reaction between an esterified polysaccharide and a polyamine are disclosed in Patent Publication No. WO94/23832. The particles include at least one esterified polysaccharide and at least one polyamine, as well as at least one gellable polysaccharide when neither the esterified polysaccharide nor the polyamine can be gelled under the selected operating conditions. Said particle includes, at least on its surface, a membrane consisting of the product of the trans-acylation reaction between the esterified polysaccharide and said polyamine within an optionally gellable gel, said reaction causing the formation of covalent amide bonds. Such particles may be used to encapsulated various active principles useful in the fields of cosmetics, pharmaceuticals and agri-foodstuffs, enzymes, cells and micro-organisms.

Microcapsule and micromatrix bodies and method for their formation are taught in U.S. Pat. No. 4,931,362. An organic phase which comprises a water-insoluble material to be encapsulated, a capsule-forming or matrix-forming monomer or prepolymer and, should this be desirable, a solvent, is dispersed in droplet form in an aqueous phase. The capsule-forming or matrix-forming monomer or prepolymer forms a sheath around the material to be encapsulated. As a capsule-forming or matrix-forming monomer, an organosilicon compounds are used. The method can be carried out easily and requires only one compound to form the capsules or micromatrix bodies. In the implementation of the method, no foam occurs and the method results in end products with an acceptable shelf life.

Preparation of biodegradable microspheres useful as carriers for macromolecules is taught in U.S. Pat. No. 4,741,872, which discloses a method for preparing biodegradable microspheres having a three-dimensional network in which biologically active macromolecular agents are physically entrapped therein. The microsphere is able to degrade and release the macromolecular agent at a controlled rate. The method involves emulsifying a vinyl derivative of a biodegradable hydrophilic polymer, a water-soluble monovinyl monomer and a biologically active macromolecule in water, and copolymerizing the biodegradable hydrophilic polymer and the water-soluble monovinyl monomer such that the biologically active macromolecule is entrapped therein.

However, there are still some problems associated with the use of microcapsules to transport active pharmaceutical ingredient. Up to now, little attention has been devoted to the design and manufacture of capsules comprising active pharmaceutical ingredient with well-defined surfaces equipped with a plurality of various chemical groups.

SUMMARY OF THE INVENTION

The present invention relates a microcapsule that comprises a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises either (a) a surface functional group selected from the group consisting of —OH, —COOH, —NH$_2$, —NHR" and a protected form thereof, wherein R" is a $C_1$ to $C_7$ hydrocarbon group; or (b) a reaction product of the surface functional group with a reactant.

The present invention also relates to a method of preparing microcapsules comprising the steps of (a) dissolving or suspending at least one water-soluble monomer comprising at least two polymerization functional groups selected from the group consisting of hydroxyl, carboxylic acid, primary amine, secondary amine, alkene, and alkyne in a polar solvent to prepare a polar solution; (b) dissolving or suspending at least one oil-soluble monomer comprising at least two polymerization functional groups selected from the group consisting of a halide, acyl halide, sulfonyl halide, isocyanate, and isothiocyanate, and azide in pharmaceutically acceptable oil to prepare an oil solution; wherein either the aqueous solution or the oil solution further comprises an active pharmaceutical ingredient; and wherein either the water-soluble monomer or the oil soluble monomer further comprises a surface functional group selected from the group consisting of —OH, —COOH, —NH$_2$, —NHR" and a protected form thereof, wherein R" is a $C_1$ to $C_7$ hydrocarbon group; and (c) contacting the polar solution with the oil solution to form a microcapsule comprising a core encapsulated by a shell, wherein the core comprises the active pharmaceutical ingredient and the shell comprises a polymer selected from a group consisting of polyether, polyester, polyamine, polyamide, polyurea, polyurethane, polythiocarbamate, polythiocarbonate, and triazole; and wherein the shell further comprises an outer surface of the shell, wherein the outer surface comprises a plurality of the surface functional groups.

Further the present invention relates to a method of preparing microcapsules comprising an active pharmaceutical ingredient, by interfacial condensation polymerization of at least two monomers, wherein at least one monomer comprises at least one surface functional selected from the group consisting of —OH, —COOH, —NH$_2$, —NHR" and a protected form thereof, wherein R" is a $C_1$ to $C_7$ hydrocarbon group; that does not react in the condensation polymerization to form a microcapsule comprising the surface functional group.

The present invention relates to functionalized microcapsules in sub-millimeter sizes. The microcapsules are approximately spherical. The microcapsules have a diameter less than 1 mm, but otherwise are not limited by its size, and may be described as microspheres or nanocapsules. The preferred size of capsules of the invention is between 50 nanometers and 10 micrometers.

To control the microcapsules size when using interfacial condensation polymerization, appropriate reaction conditions need to be selected. Generally, greater the amount of energy that is introduced into the reaction mixture, smaller the size of the microcapsule. The energy may be delivered thermally, through heating, by vigorous stirring or via sonication.

The outer surface of the microcapsules shell of the present invention further comprises one or more of one or more type of chemical functional groups that can then be reacted further. The surface functional groups are selected from the group consisting of —OH, —COOH, —NH$_2$, —NHR" and a protected form thereof, wherein R" is a $C_1$ to $C_7$ hydrocarbon group.

The microcapsules are prepared by interfacial polymerization. Under one embodiment of the present invention the interfacial polymerization is interfacial condensation polymerization. Under another embodiment, the interfacial polymerization is interfacial addition polymerization.

The mixture may be an oil in water dispersion or a water in oil dispersion. Thus, the prepared microcapsules may have a core that comprises either water or oil.

In addition to the above-described three-step process, the present invention is also directed to a two-step process. Under the two step process of preparing microcapsules according to another embodiment of the present invention, comprises the steps of (a) mixing of at least water, pharmaceutically acceptable oil, active pharmaceutical ingredient, a surfactant, and a water-soluble monomer comprising at least two polymerization functional groups selected from the group consisting of hydroxyl, carboxylic acid, primary amine, secondary amine, alkene, and alkyne to prepare homogeneous dispersion; and (b) adding at least one oil-soluble monomer comprising at least two polymerization functional groups selected from the group consisting of a halide, acyl halide, sulfonyl halide, isocyanate, and isothiocyanate, and azide in pharmaceutically acceptable oil to prepare an oil solution; wherein the water-soluble monomer or the oil soluble monomer or both further comprises a surface functional group selected from the group consisting of —OH, —COOH, —NH$_2$, —NHR" and a protected form thereof, wherein R" is a $C_1$ to $C_7$ hydrocarbon group.

In both the three-step and the two-step methods of preparing the microcapsule, it is useful to mix or agitate the mixture vigorously. This addition of energy to the mixture yields smaller microcapsules and uniform microcapsules.

Under interfacial condensation polymerization technique, a shell is formed on the surface of droplets (oil in water or water in oil) when water-soluble monomers react with oil-soluble monomers. It is also important that neither the water-soluble monomer nor the oil-soluble monomer react with any of the solvents used to prepare the microcapsules, nor with the active pharmaceutical ingredient.

The water-soluble monomers comprise a plurality of polymerization functional groups. The oil-soluble monomers comprise a plurality of polymerization functional groups. The polymerization functional groups on the water-soluble monomers react with the polymerization functional groups on the oil-soluble monomers to form the polymeric shell.

Generally, the mean number of polymerization functional groups on the water-soluble monomer and on the oil-soluble monomer is 2 or more. Under one embodiment, the mean number of polymerization functional groups on the water-soluble monomer is about 2.0 to about 2.5 per water-soluble monomer.

The monomeric compounds that contain the above polymerization functional groups are organic compounds. Such organic compounds are generally inert with respect to the interfacial condensation polymerization, and should not negatively affect the polymerization.

In addition to the polymerization functional groups, selected monomers involved in the formation of the shell also comprise surface functional groups, i.e., groups that are not involved in the formation of the shell of the microcapsule, but rather is a functional group that after the formation of the shell is found on the surface of the shell.

It is important that the surface functional groups be selected so that they do not interfere with the condensation reaction forming the capsules' shell. This may be done by having protecting groups present on the functional groups during the interfacial condensation polymerization, and subsequently deprotecting the functional groups.

One example of forming a microcapsule comprising a shell wherein the shell comprises a surface functional group, is where one of the monomers (either the water-soluble monomer or the oil-soluble monomer) comprises the surface functional group. This example can be generalized by the equation in FIG. 4, wherein the monomers are represented by the zigzag lines; X and Y at the end of the monomers each represent a polymerization functional group; the XY group represent a group formed from the reaction of the X polymerization functional group and Y polymerization functional group; the annulus represents the spherical shell of the microcapsule, and A is a surface functional group.

The present invention is also directed to a microcapsule comprising a shell that comprises several kinds of surface functional groups. An example of forming a microcapsule comprising a shell wherein the shell comprises two types of surface functional groups, is where one of the monomers (either the water-soluble monomer or the oil-soluble monomer) comprises one surface functional group, and the other monomer comprises a different functional group. In this example, the surface comprises two different kinds of surface functional groups. This example can be generalized by the equation in FIG. 7, wherein the symbols are as represented previously and wherein B is different surface functional group.

Preparation of microcapsules comprising a shell comprising multiple numbers of surface functional groups is also possible. Because kinetics of reactions of polymerization usually do not depend on the type of the non-reactive groups present, it is possible to control the quantities of various monomers entering into the reactions of the formation of the shell. Thus, the compounds containing the same polymerization functional groups and different surface functional groups may be mixed in required proportions. Forming a microcapsule comprising a shell wherein the shell comprises several different surface functional groups, may be achieved by using one of the monomers (either the water-soluble monomer or the oil-soluble monomer) which comprise a mixture two or more different monomeric compounds that contain different surface functional groups. This example can be generalized by the equation in FIG. 9, wherein the symbols are as represented previously, wherein A, B, and C are different surface functional group.

Generally, the surface functional groups are different from either of the two polymerization functional groups present on the water-soluble and oil-soluble monomers. The surface functional group must not react with either of the two polymerization functional groups in any significant amount. However, one of the aspects of the present invention is the placement of surface functional group on the shell that is identical to one of the polymerization functional groups, by using protecting groups.

The microcapsule as described above contains surface functional groups selected from the group consisting of —OH, —COOH, —NH$_2$, —NHR" and a protected form thereof, wherein R" is a $C_1$ to $C_7$ hydrocarbon group. Under one embodiment, the microcapsule may be isolated, and formulated into a medical composition. Under another embodiment, the microcapsule may be reacted further with a reactant, so that the reactant may be grafted onto the surface of the microcapsule via the surface functional group.

The present invention is also directed to a method of modifying the microcapsules comprising surface functional groups by performing reactions with the surface functional groups. In such a way, different groups may be grafted onto the surface of the microcapsule.

The surface functional groups are reacted with a reactant, in which the reactant residue is grafted onto the surface of the microcapsule. This may be illustrated as in FIG. 11, wherein —OH is a hydroxyl group exemplifying a surface functional group; RCl is an alkyl halide that exemplifies a reactant that can be grafted onto the surface of the microcapsule through an ether bond. The R is the reactant residue of the reactant RCl, or "graft".

The present invention also allows to selectively react the surface functional group with reactants. Under one embodiment, the microcapsule comprises surface functional groups wherein a limited number of surface functional groups ("minor groups") are different from the grafted surface functional groups ("major groups") on the microcapsule. This is achieved by reacting the formed microcapsule onto a substrate via bonds to a minor amount of the surface functional groups reacted further those surface functional groups not used in the bonding to the substrate, and decoupling the microcapsule from the flat surface to produce a capsules comprising minor surface functional groups and major surface functional groups.

The selection of the surface functional groups, and the grafts have a great impact on the physical and chemical properties of the microcapsules, and thus on the efficacy of the drug. The transport properties of microcapsules are affected by the hydrophilicity of the microcapsules. The hydrophilicity of microcapsules can be increased by increasing the number of hydrophilic groups on the surface of the microsphere. Such hydrophilic groups include hydroxyl, carboxylic acid, and sulfonic acid groups. Such hydrophilic groups may be either a surface functional group (i.e., they were present on the monomer), or they may be present on the graft. Nonionic moieties, like those of polyethylene glycol, polypropylene glycol or those deriving from protected carbohydrates can be used.

In some applications of the present invention, it may be beneficial to introduce the active pharmaceutical ingredient by multiple means that may require a series of different surface groups. A mixture of microcapsules may be introduced to the patient.

The present invention is also directed to a medical composition comprising the microcapsule. The medical composition is used to administer the active pharmaceutical ingredient to a patient in need of the active pharmaceutical ingredient. The medical composition comprising microcapsule can be administered in any of the typical routes of administration, including enteral, parenteral, oral, intravenous, rectal, topical, sublingual, subcutaneous, or by inhalation.

An aqueous form of the medical composition comprising the microcapsules of the present invention may optionally comprise anticoagulants. Anticoagulants may be used to mitigate clumping of microcapsules which may be present due to the surface properties of the microcapsules.

Under one embodiment of the present invention, the release of active pharmaceutical ingredient from the microcapsule of the present invention is similar to the release of active pharmaceutical ingredient from microcapsules as known in the art. One form of such release is a controlled release over time. Such a release may be a slow diffusion of the active pharmaceutical ingredient through the shell. Another form of release is by rupturing of the shell and disgorging the contents of the core including the active pharmaceutical ingredient. The release of the active pharmaceutical ingredient from the capsule might be triggered by a pH change, presence of certain enzymes at the location, an exposure to ultrasound, or an exposure to a magnetic field.

Triggering of release by enzymes may be accomplished by the enzymes breaking bonds within the shell. For example, such enzymes may hydrolyze the ester or amide bonds of the polyester or polyamide polymer of the shell.

The invention is defined by at least thirty-seven aspects.

In the first aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a $C_1$ to $C_7$ hydrocarbon group.

In the second aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a $C_1$ to $C_7$ hydrocarbon group, wherein the polymeric shell is formed by an interfacial condensation polymerization process.

In the third aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a $C_1$ to $C_7$ hydrocarbon group; wherein the polymeric shell is formed by the reaction of at least one water-soluble monomer comprising at least two polymerization functional groups selected from the group consisting of hydroxyl, phenoxyl, carboxylic acid, primary amine, secondary amine, sulfonic acid, alkene, and alkyne; and at least one oil-soluble monomer, comprising at least two polymerization functional groups selected from the group consisting of a halide, acyl halide, sulfonyl halide, isocyanate, isothiocyanate, thiol, and azide; wherein the water-soluble monomer or the oil-soluble monomer or both, further comprises at least one surface functional group.

In the fourth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a $C_1$ to $C_7$ hydrocarbon group; wherein the polymeric shell is formed by the reaction of at least one water-soluble monomer comprising at least two polymerization functional hydroxyl groups; and at least one oil-soluble monomer, comprising at least two polymerization functional groups selected from the group consisting of a halide, acyl halide, sulfonyl halide, isocyanate, and isothiocyanate.

In the fifth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a $C_1$ to $C_7$ hydrocarbon group; wherein the polymeric shell is formed by the reaction of at least one water-soluble monomer comprising at least two polymerization functional primary amine groups; and at least one oil-soluble monomer comprising at least two polymerization functional groups selected from the group consisting of a halide, acyl halide, sulfonyl halide, isocyanate, and isothiocyanate.

In the sixth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a $C_1$ to $C_7$ hydrocarbon group; wherein the polymeric shell is formed by the reaction of at least one water-soluble diacid; and at least one oil-soluble dihalide.

In the seventh aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a $C_1$ to $C_7$ hydrocarbon group; wherein the polymeric shell is formed by the reaction of at least one water-soluble diacid; and at least one oil-soluble dihalide selected from the group consisting of 1,2-bis(bromomethyl)benzene, 1,3-bis(bromomethyl)benzene, 1,4-bis(bromomethyl)benzene, 1,2-bis(chloromethyl)benzene, 1,3-bis(chloromethyl)benzene, 1,4-bis(chloromethyl)benzene, and mixtures thereof.

In the eighth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one water-soluble monomer comprising at least two polymerization functional hydroxyl groups; and at least one oil-soluble monomer comprising at least two acyl halide polymerization functional groups.

In the ninth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one water-soluble monomer comprising at least two primary amine polymerization functional groups; and at least one oil-soluble monomer comprising at least two acyl halide polymerization functional groups.

In the tenth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one water-soluble monomer comprising at least two polymerization functional groups selected from the group consisting of primary amine and hydroxyl; and at least one oil-soluble monomer comprising at least two polymerization sulfonyl halide functional groups.

In the eleventh aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one water-soluble monomer comprising at least two polymerization functional groups selected from the group consisting of primary amine group and hydroxyl; and at least one oil-soluble monomer comprising at least two isocyanate polymerization functional groups.

In the twelfth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one water-soluble monomer comprising at least two polymerization functional groups selected from the group consisting of primary amine group and hydroxyl group; and at least one oil-soluble monomer comprising at least two isothiocyanate polymerization functional groups.

In the thirteenth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one water-soluble monomer comprising at least two alkyne polymerization functional groups; and at least one oil-soluble monomer comprising at least two azide polymerization functional groups.

In the fourteenth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one oil-soluble monomer comprising at least two polymerization functional groups selected from the group consisting of hydroxyl, phenoxyl, carboxylic acid, primary amine, secondary amine, sulfonic acid, and alkyne; and at least one oil-soluble monomer, comprising at least two polymerization functional groups selected from the group consisting of a halide, acyl halide, isocyanate, thiol, and azide; wherein the oil-soluble monomer or the water-soluble monomer or both, further comprises at least one surface functional group.

In the fifteenth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one oil-soluble monomer comprising at least two polymerization functional hydroxyl groups; and at least one water-soluble monomer, comprising at least two polymerization functional groups selected from the group consisting of a halide, acyl halide, and isocyanate.

In the sixteenth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one oil-soluble monomer comprising at least two polymerization functional primary amine groups; and at least one water-soluble monomer comprising at least two polymerization functional groups selected from the group consisting of a halide, acyl halide, and isocyanate.

In the seventeenth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one oil-soluble diacid; and at least one water-soluble dihalide.

In the eighteenth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one oil-soluble monomer comprising at least two polymerization functional hydroxyl groups; and at least one water-soluble monomer comprising at least two acyl halide polymerization functional groups.

In the nineteenth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one oil-soluble monomer comprising at least two primary amine polymerization functional groups; and at least one water-soluble monomer comprising at least two acyl halide polymerization functional groups.

In the twentieth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one oil-soluble monomer comprising at least two polymerization functional groups selected from the group consisting of primary amine and hydroxyl; and at least one water-soluble monomer comprising at least two polymerization sulfonyl halide functional groups.

In the twenty-first aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; wherein the polymeric shell is formed by the reaction of at least one oil-soluble monomer comprising at least two polymerization functional groups selected from the group consisting of primary amine group and hydroxyl; and at least one water-soluble monomer comprising at least two isocyanate polymerization functional groups.

In the twenty-second aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and polytriazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a $C_1$ to $C_7$ hydrocarbon group; wherein the polymeric shell is formed by the reaction of at least one oil-soluble monomer comprising at least two alkyne polymerization functional groups; and at least one water-soluble monomer comprising at least two azide polymerization functional groups.

In the twenty-third aspect, the present invention relates to a microcapsule comprising a core encapsulated by a polymeric shell, wherein the core comprises an active pharmaceutical ingredient and a pharmaceutically acceptable oil; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —$NH_2$, —NHR", a protected form of the foregoing, and a mixture of the foregoing, wherein R" is a $C_1$ to $C_7$ hydrocarbon group.

In the twenty-fourth aspect, the present invention relates to a microcapsule comprising a core encapsulated by a polymeric shell, wherein the core comprises an active pharmaceutical ingredient and water; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —$NH_2$, —NHR", a protected form of the foregoing, and a mixture of the foregoing, wherein R" is a $C_1$ to $C_7$ hydrocarbon group.

In the twenty-fifth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —$NH_2$, —NHR", a protected form of the foregoing, and a mixture of the foregoing, wherein R" is a $C_1$ to $C_7$ hydrocarbon group, wherein the mean diameter of the microcapsule is less than 500 micrometers.

In the twenty-sixth aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —$NH_2$, —NHR", a protected form of the foregoing, and a mixture of the foregoing, wherein R" is a $C_1$ to $C_7$ hydrocarbon group, wherein the mean diameter of the microcapsule is less than 10 micrometers.

In the twenty-seventh aspect, the present invention relates to a microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —$NH_2$, —NHR", a protected form of the foregoing, and a mixture of the foregoing, wherein R" is a $C_1$ to $C_7$ hydrocarbon group; wherein the mean diameter of the microcapsule is less than 50 nanometers.

In the twenty-eighth aspect, the present invention relates to a medical composition for use in administration to a patient comprising the microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —$NH_2$, —NHR", a protected form of the foregoing, and a mixture of the foregoing, wherein R" is a $C_1$ to $C_7$ hydrocarbon group.

In the twenty-ninth aspect, the present invention relates to a medical composition for use in administration to a patient comprising the microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —$NH_2$, —NHR", a protected form of the foregoing, and a mixture of the foregoing, wherein R" is a $C_1$ to $C_7$ hydrocarbon group; wherein the medical composition is administered orally, intravenously, rectally, sublingually, or subcutaneously.

In the thirtieth aspect, the present invention relates to a grafted microcapsule comprising a reaction product of the microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —$NH_2$, —NHR", a protected form of the foregoing, and a mixture of the foregoing, wherein R" is a $C_1$ to $C_7$ hydrocarbon group; and a reactant of formula RZ, wherein Z is selected from a group consisting of halide, acyl halide, sulfonyl halide, anhydride, azide, thio, isocyanate, and isothiocyanate; and R is an organic group selected from the group consisting of a hydrophilic group, a thiosugar, a monosaccharide, an oligosaccharide, a polysaccharide, a protein, and a hydrophobic group.

In the thirty-first aspect, the present invention relates to a medical composition for use in administration to a patient comprising a grafted microcapsule comprising a reaction product of the microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; and a reactant of formula RZ, wherein Z is selected from a group consisting of halide, acyl halide, sulfonyl halide, anhydride, azide, thio, isocyanate, and isothiocyanate; and R is an organic group selected from the group consisting of a hydrophilic group, a thiosugar, a monosaccharide, an oligosaccharide, a polysaccharide, a protein, and a hydrophobic group.

In the thirty-second aspect, the present invention relates to a medical composition for use in administration to a patient comprising a grafted microcapsule comprising a reaction product of the microcapsule comprising a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises a surface functional group selected from the group consisting of —OH, —COOH, —NH$_2$, —NHR", a protected form of the foregoing, and a mixture of the foregoing, wherein R" is a C$_1$ to C$_7$ hydrocarbon group; and a reactant of formula RZ, wherein Z is selected from a group consisting of halide, acyl halide, sulfonyl halide, anhydride, azide, thio, isocyanate, and isothiocyanate; and R is an organic group selected from the group consisting of a hydrophilic group, a thiosugar, a monosaccharide, an oligosaccharide, a polysaccharide, a protein, and a hydrophobic group; wherein the medical composition is administered orally, intravenously, rectally, sublingually, or subcutaneously.

In the thirty-third aspect, the present invention relates to a method of preparing microcapsules comprising the steps of dissolving or suspending at least one water-soluble monomer comprising at least two polymerization functional groups selected from the group consisting of hydroxyl, carboxylic acid, primary amine, secondary amine, alkene, and alkyne in a polar solvent to prepare a polar solution; dissolving or suspending at least one oil-soluble monomer comprising at least two polymerization functional groups selected from the group consisting of a halide, acyl halide, sulfonyl halide, isocyanate, and isothiocyanate, and azide in a non-polar solvent to prepare a non-polar solution; wherein either the polar solution or the non-polar solution further comprises an active pharmaceutical ingredient; and wherein either the water-soluble monomer or the monomer soluble in a non-polar solvent further comprises a surface functional group selected from the group consisting of —OH, —COOH, —NH$_2$, —NHR" and protected form thereof, wherein R" is a C$_1$ to C$_7$ hydrocarbon group; and contacting the polar solution with the non-polar solution to form a microcapsule comprising a core encapsulated by a shell, wherein the core comprises the active pharmaceutical ingredient and the shell comprises a polymer selected from a group consisting of polyether, polyester, polyamine, polyamide, polyurea, polyurethane, polythiocarbamate, polythiocarbonate, and polytriazole; and wherein the shell further comprises an outer surface of the shell, wherein the outer surface comprises a plurality of the surface functional groups.

In the thirty-fourth aspect, the present invention relates to a method of preparing microcapsules comprising the steps of dissolving or suspending at least one oil-soluble monomer comprising at least two polymerization functional groups selected from the group consisting of hydroxyl, phenol, carboxylic acid, primary amine, secondary amine, sulfonic acid, and alkyne in a non-polar solvent to prepare a non-polar solution; dissolving or suspending at least one water-soluble monomer comprising at least two polymerization functional groups selected from the group consisting of a halide, acyl halide, isocyanate, thiol, and azide in a polar solvent to prepare a polar solution; wherein either the polar solution or the non-polar solution further comprises an active pharmaceutical ingredient; and wherein either the oil-soluble monomer or the water-soluble monomer further comprises a surface functional group selected from the group consisting of —OH, —COOH, —NH$_2$, —NHR" and protected form thereof, wherein R" is a C$_1$ to C$_7$ hydrocarbon group; and contacting the polar solution with the non-polar solution to form a microcapsule comprising a core encapsulated by a shell, wherein the core comprises the active pharmaceutical ingredient and the shell comprises a polymer selected from a group consisting of polyether, polyester, polyamine, polyamide, polyurea, polyurethane, polythiocarbamate, polythiocarbonate, and polytriazole; and wherein the shell further comprises an outer surface of the shell, wherein the outer surface comprises a plurality of the surface functional groups.

In the thirty-fifth aspect, the present invention relates to a method of preparing microcapsules comprising an active pharmaceutical ingredient, by interfacial condensation polymerization of at least two monomers, wherein at least one monomer comprises at least one surface functional selected from the group consisting of —OH, —COOH, —NH$_2$, —NR", and a protected form thereof, wherein R is a C$_1$ to C$_7$ hydrocarbon group, that does not react in the condensation polymerization to form a microcapsule comprising the surface functional group.

In the thirty-sixth aspect, the present invention relates to a method of preparing microcapsules comprising an active pharmaceutical ingredient, by interfacial condensation polymerization of at least two monomers, wherein at least one monomer comprises at least one surface functional selected from the group consisting of —OH, —COOH, —NH$_2$, —NR", and a protected form thereof, wherein R is a C$_1$ to C$_7$ hydrocarbon group, that does not react in the condensation polymerization to form a microcapsule comprising the surface functional group, wherein the method comprises the steps of mixing of at least water, pharmaceutically acceptable oil, active pharmaceutical ingredient, a surfactant, and a water-soluble monomer comprising at least two polymerization functional groups selected from the group consisting of hydroxyl, carboxylic acid, primary amine, secondary amine, alkene, and alkyne to prepare homogeneous dispersion; and adding at least one oil-soluble monomer comprising at least two polymerization functional groups selected from the group consisting of a halide, acyl halide, sulfonyl halide, isocyanate, and isothiocyanate, and azide; wherein the water-soluble monomer or the oil soluble monomer or both further comprises a surface functional group selected from the group consisting of —OH, —COOH, —NH$_2$, —NHR", and protected form thereof, wherein R" is a C$_1$ to C$_7$ hydrocarbon group.

In the thirty-seventh aspect, the present invention relates to a method of preparing microcapsules comprising an active pharmaceutical ingredient, by interfacial condensation polymerization of at least two monomers, wherein at least one monomer comprises at least one surface functional selected from the group consisting of —OH, —COOH, —NH$_2$, —NR", and a protected form thereof, wherein R is a $C_1$ to $C_7$ hydrocarbon group, that does not react in the condensation polymerization to form a microcapsule comprising the surface functional group, wherein the method comprises the steps of mixing of at least water, pharmaceutically acceptable oil, active pharmaceutical ingredient, a surfactant, and an oil-soluble monomer comprising at least two polymerization functional groups selected from the group consisting of hydroxyl, carboxylic acid, primary amine, secondary amine, alkyne, to prepare homogeneous dispersion; and adding at least one water-soluble monomer comprising at least two polymerization functional groups selected from the group consisting of a halide, acyl halide, sulfonyl halide, isocyanate, and isothiocyanate, and azide, and; wherein the water-soluble monomer or the oil soluble monomer or both further comprises a surface functional group selected from the group consisting of —OH, —COOH, —NH$_2$, —NHR", and protected form thereof, wherein R" is a $C_1$ to $C_7$ hydrocarbon group.

BRIEF DESCRIPTION OF THE DRAWINGS

The features and advantages of the various embodiments disclosed herein will be better understood with respect to the following description and drawings. The exemplary embodiments of the invention are illustrated in the drawings and explained further hereinunder.

DETAILED DESCRIPTION OF THE INVENTION

Figure 1:
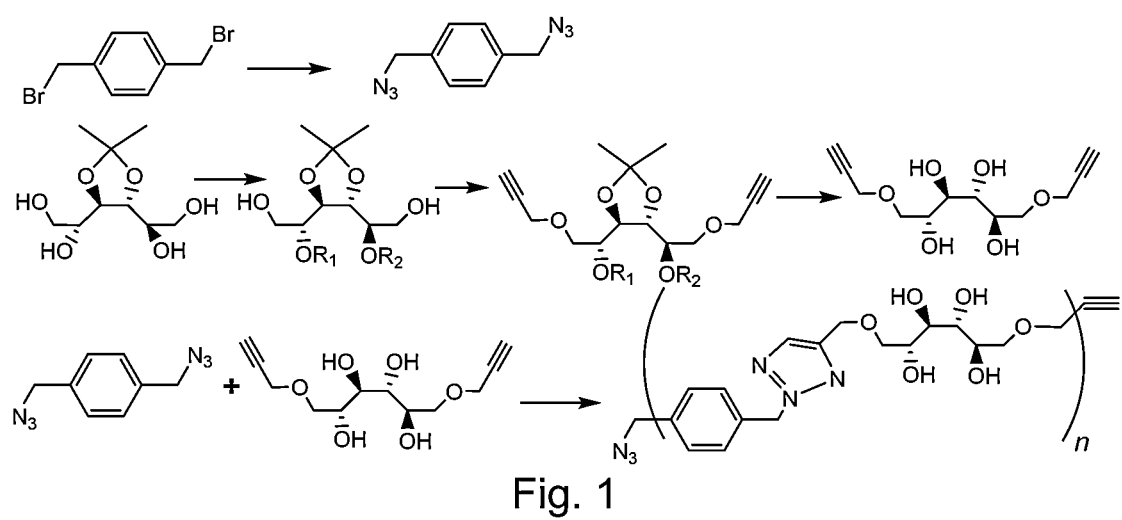
FIG. 1 is a specific example of the use of click chemistry to prepare microcapsules.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

The present invention relates a microcapsule that comprises a core encapsulated by a polymeric shell, wherein the core comprises an active pharmaceutical ingredient; the polymeric shell comprises polymeric material selected from the group consisting of polyether, polyester, polyamine, polyamide, polyurea, polyurethane, polythiocarbamate, polythiocarbonate, and triazole; and the shell comprises an inner surface and an outer surface, wherein the outer surface comprises either (a) a surface functional group selected from the group consisting of —OH, —COOH, —NH$_2$, —NHR" and a protected form thereof, wherein R" is a $C_1$ to $C_7$ hydrocarbon group; or (b) a reaction product of the surface functional group with a reactant, or (c) a combination thereof.

The present invention also relates to a method of preparing microcapsules comprising the steps of (a) dissolving or suspending at least one water-soluble monomer comprising at least two polymerization functional groups selected from the group consisting of hydroxyl, carboxylic acid, primary amine, secondary amine, azide, acyl halide, alkene, and alkyne in a polar solvent to prepare a polar solution; (b) dissolving or suspending at least one oil-soluble monomer comprising at least two polymerization functional groups selected from the group consisting of a halide, acyl halide, sulfonyl halide, isocyanate, isothiocyanate, azide, acid, and diol in a non-polar solvent to prepare a non-polar solution; wherein either the polar solution or the non-polar solution further comprises an active pharmaceutical ingredient; and wherein either the water-soluble monomer or the oil-soluble monomer further comprises a surface functional group selected from the group consisting of —OH, —COOH, —NH$_2$, —NHR" and a protected form thereof, wherein R" is a $C_1$ to $C_7$ hydrocarbon group; and (c) contacting the polar solution with the non-polar solution to form a microcapsule comprising a core encapsulated by a shell, wherein the core comprises the active pharmaceutical ingredient and the shell comprises a polymer selected from a group consisting of polyether, polyester, polyamine, polyamide, polyurea, polyurethane, polythiocarbamate, polythiocarbonate, and triazole; and wherein the shell further comprises an outer surface of the shell, wherein the outer surface comprises a plurality of the surface functional groups.

Further, the present invention relates to a method of preparing microcapsules comprising an active pharmaceutical ingredient, by interfacial condensation polymerization of at least two monomers, wherein at least one monomer comprises at least one surface functional selected from the group consisting of —OH, —COOH, —NH$_2$, —NHR" and a protected form thereof, wherein R" is a $C_1$ to $C_7$ hydrocarbon group, that does not react in the condensation polymerization to form a microcapsule comprising the surface functional group.

One of the advantages of functionalized microcapsules in delivering an active pharmaceutical ingredient is that it allows for delivery of the active pharmaceutical ingredient regardless of the solubility of the active pharmaceutical ingredient in bodily fluids. Insoluble drugs or poorly soluble drugs may be encapsulated, and with the appropriately functionalized surface can be transported throughout blood, spinal fluids, or other bodily fluids to be delivered to the target organ.

Another advantage of using functionalized microcapsules in delivering active pharmaceutical ingredient is the ability of designing the functional groups to be recognized by specific receptors. The necessary chemical functionalities may be present on the capsules surface, and do not have to affect the structure of the drug.

Yet another advantage of using functionalized microcapsules in delivering active pharmaceutical ingredient is the greater drug-to-receptor ratio. When an active compound is conjugated directly to a selected functional group, the molar ratio of the drug to the functional group is usually 1:1 or at times 2:1. However, when an active compound is encapsulated, the number of groups coupled to the surface is usually significantly higher than the number of capsules, but much smaller than the number of molecules of the active inside the microcapsule. Consequently, a small number of receptors can attract a small number of conjugated compounds, or a small number of capsules, but a very large number of molecules of the encapsulated drug.

Still another advantage of using functionalized microcapsules in delivering active pharmaceutical ingredient is due to the ease of selecting the required functional groups. Due to the chemical and structural nature of the active pharmaceutical ingredient, only certain functional groups may be used conjugated with any one active pharmaceutical ingredient. However, because the design and chemical structure of the capsules' surface can be such that it is the most convenient for the given application, it is generally easier to couple the required functionalities to the capsules' surface than to couple the same functionalities directly to the molecules of the active compound.

A further advantage of using functionalized microcapsules in delivering active pharmaceutical ingredient is the advantage in using a number of different functional groups on the surface of the shell. An active pharmaceutical ingredient generally has a very limited number of chemical "handles" that one can take advantage of and couple several different functional groups. However, microcapsules are much larger than molecules of the active pharmaceutical ingredient, it is possible to have many "handles" on the surface of the microcapsules, and thus, attach several different functional groups facilitating transport to the target organ in the body.

Yet a further advantage of using functionalized microcapsules in delivering active pharmaceutical ingredient is that the method of manufacturing capsules with a multifunctional surface via interfacial condensation polymerization allows for a good control of shell characteristics, such as the shell thickness. By judiciously selecting reaction components and conditions that control the shell characteristics, it is possible to control the place and rate of microcapsules' release of the active pharmaceutical ingredient. To improve the efficacy of the active pharmaceutical ingredient, the release may takes place close to the location, or the rate of the release is matched to the rate of the active pharmaceutical ingredient reaction with the specific receptors, or both.

A still further advantage of using functionalized microcapsules in delivering active pharmaceutical ingredient is the lower need for the active pharmaceutical ingredient. When the release takes place at a targeted location and the release kinetics is controlled, then much less of the active pharmaceutical ingredient is needed. Using substantially less active pharmaceutical ingredient improves the economics of the drug's application, and reduces side effects for the patient. This is especially useful for drugs that are efficacious but are thought to have undesirable side effects, such as thiazolidinedione, paroxetine, fluoxetine, venlafaxine, sertraline, escitalopram, valproic acid, drospirenone, isotretinoin, dabigatran, rivaroxaban, alendronic acid, and finasteride.

Moreover, there are additional advantages of delivering the active pharmaceutical ingredient by the microcapsules of the present invention.

One advantage of using functionalized microcapsules in delivering active pharmaceutical ingredient is the protection of the active pharmaceutical ingredient from compounds present in the environment and other drugs during transport within the body.

Another advantage of using functionalized microcapsules in delivering active pharmaceutical ingredient is that the same methodology of making microcapsules and microcapsule surface design are applicable to a variety of drugs.

Yet another advantage of using functionalized microcapsules in delivering active pharmaceutical ingredient is that molecules of the active compound inside the capsule can be kept in the most suitable medium (for example, in a specific buffer) and not in the varying environment of the body.

Still another advantage of using functionalized microcapsules in delivering active pharmaceutical ingredient is that the payload release may be accomplished either remotely (for example, by using focused ultrasound) or by a change in the capsules environment. Frequently it is easier to break bonds forming the capsules shell to release the active compound rather than to decouple chemical moieties connected via a covalent bond as in case for drug-protein or drug-carbohydrate conjugates.

A further advantage of using functionalized microcapsules in delivering active pharmaceutical ingredient is that the active compound is ready to act at the moment of its release.

Yet further advantage of using functionalized microcapsules in delivering active pharmaceutical ingredient is that it is relatively easy to accomplish the release of two or more active compounds at the same time and at a location using either different capsules or capsules containing more than one active pharmaceutical ingredient.

Another further advantage of using functionalized microcapsules in delivering active pharmaceutical ingredient is the ability to use ferromagnetic units on the surface of the microcapsules. Coupling various compounds to magnetic beads is known to be used of diagnostic procedures, but it is considered problematic to employ drug molecules conjugated to magnetic beads for therapeutic purposes. The microcapsules of the present invention may be modified to introduce ferromagnetic units onto the surface of microcapsules and take advantage of the capsules magnetic properties during transport or in aiding in the microcapsules destination and rupture.

As used herein and in the appended claims, the singular forms "a", "an", and "the" include plural references unless the context clearly dictates otherwise. The singular form of any class of the ingredients refer not only to one chemical species within that class, but also to a mixture of those chemical species; for example, the term "solvent" in the singular form may refer to a mixture of compounds each of which is also a solvent. The terms "a" (or "an"), "one or more" and "at least one" can be used interchangeably herein. It is also to be noted that the terms "comprising", "including", and "having" can be used interchangeably.

The abbreviations and symbols as used herein, unless indicated otherwise, take their ordinary meaning. The abbreviation "RPM" means rotations per minute. The abbreviation or symbol "mmol" means millimoles. The abbreviation or symbol "mL" means milliliters. The abbreviation or symbol "mg" means milligrams. The abbreviation or symbol "mm" means millimeter. The abbreviation or symbol "μm" means micrometer. The abbreviation or symbol "nm" means nanometer.

The term "about" when referring to a number means ±3%. For example, the phrase "about 50" refers to a number between and including 48.500 and 51.500.

The term to "encapsulate" means to surround, encase, or protect in a microcapsule.

The term "microcapsule" means and includes a particle of active compound encapsulated within a shell of a polymeric material. The definition of the term "microcapsule" includes a nanocapsule. The definition of the term "microcapsule" includes a microsphere. Unless stated otherwise, the term "microcapsule" refers to multicore, single-core, or a mixture of multicore and single-core microcapsules. Under one embodiment, the term "microcapsule" refers to a matrix microcapsule. Under another embodiment, the term "microcapsule" refers to a reservoir microcapsule.

The term "size" when referring to a microcapsule, means the volume mean diameter of the microcapsule, D[4,3]. The volume mean diameter D[4,3] may be determined by any routine particle size test such as ASTM E799 (Standard Practice for Determining Data Criteria and Processing for Liquid Drop Size Analysis), using typical instruments, such as the Horiba Laser Scattering Particle Size Distribution Analyzer LA-950.

The term "shell" means and includes an assembly of a polymeric material, such as polyurea, disposed on or encapsulating a surface of a core that comprises an active ingredient. The definition of the term includes a shell that is uniform and a shell that is not uniform. The definition of the term includes a shell that completely surround the core and a shell that mostly surrounds the core.

The phrases "active pharmaceutical ingredient", "active compound" or "active ingredient" refer to one or more drugs, prodrugs, salts or esters thereof as discussed below.

The phrase "polar solution" means a solution or a solution-like mixture, wherein the solvent is polar. The phrase "non-polar solution" means a solution, or a solution-like mixture, wherein the solvent is non-polar. The phrase "solution-like mixture" means that the mixture behaves under interfacial polymerization conditions as a solution, even if the mixture is not truly a solution. For example, under one embodiment the solution-like mixture may be an emulsion or a dispersion or a mixture displaying a Tyndall effect, that under reaction conditions behaves as a solution.

The phrase "pharmaceutically acceptable" means that which is useful in preparing a pharmaceutical composition that is generally safe, non-toxic, and neither biologically nor otherwise undesirable and includes that which is acceptable for human pharmaceutical use.

For the purposes of conciseness, a list reciting chemical entities in their adjective forms implies the presence of nouns that they are modifying and of articles to make the list grammatically correct. Such an implication may be derived from the context or from the last entry in the list. For example, the phrase "polymerization functional groups selected from the group consisting of hydroxyl, carboxylic acid, primary amine, secondary amine, alkene, and alkyne" means "polymerization functional groups selected from the group consisting of a hydroxyl group, a carboxylic acid group, a primary amine group, a secondary amine group, an alkene group, and an alkyne group".

For the purpose of conciseness and clarity, chemical equations herein may show only relevant portions of the reaction, and are not necessarily balanced. For example, the equation signifying the formation of ether,

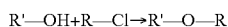

is a concise form of the reaction

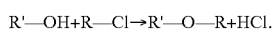

A compound is said to be "insoluble" or "substantially insoluble" in a solvent (either polar or non-polar) if it has a solubility in the solvent of less than 20 g/L. The phrase "poorly soluble" refers to the solubility of less than 50 g/L or less than 40 g/L. The solubility of the compound in the solvent is measured at ambient temperature (20° C.) and atmospheric pressure.

The present invention relates to functionalized microcapsules in sub-millimeter sizes. The microcapsules are approximately spherical. The microcapsules have a diameter less than 1 mm, but otherwise are not limited by its size, and may be described as microspheres or nanocapsules. Under one embodiment, the diameter of the microcapsule is about 10 nm to about 100 nm. Under another embodiment, the diameter of the microcapsule is about 50 nm to about 500 nm. Under still another embodiment, the diameter of the microcapsule is about 100 nm to about 1 µm. Under yet another embodiment, the diameter of the microcapsule is about 500 nm to about 5 µm. Under a further embodiment, the diameter of the microcapsule is about 1 µm to about 10 µm. Under yet still another embodiment, the diameter of the microcapsule is about 5 µm to about 50 µm. Under an additional embodiment, the diameter of the microcapsule is about 10 µm to about 100 µm. Under another additional embodiment, the diameter of the microcapsule is about 50 µm to about 500 µm. Under still another embodiment, the diameter of the microcapsule is about 100 µm to about 1 mm. Generally, diameters of less than 10 micrometers are needed in order for the microcapsule to enter the blood system. Under one embodiment the preferred size of capsules of the invention is between 50 nanometers and 10 micrometers.

To control the microcapsules size when using interfacial condensation polymerization, appropriate reaction conditions need to be selected. Generally, greater the amount of energy that is introduced into the reaction mixture, smaller the size of the microcapsule. The energy may be delivered thermally, through heating, by vigorous stirring or via sonication. The size of the microcapsule also depends on the identity and amount of the surfactant or a mixture of surfactants.

The microcapsule of the present invention comprises a shell and a core. Under one embodiment, the shell encapsulates the core fully, meaning that there is no contact between the core and the surrounding medium.

Under another embodiment, the shell encapsulates significantly, meaning that a sufficient amount of core is encapsulated to allow for contact between the core and the surrounding medium without the core leaking out of the shell. For example, the shell may comprise one or more small holes that are sufficiently small enough that the surrounding medium do not allow for the contents of the core to leak out of the microcapsule, due to either the surface tension differences between the core and the surrounding medium, or due to the viscosity of the core.

The shell comprises an outer surface and an inner surface. The concave inner surface is in contact with the core, and the convex outer surface is in the contact with the medium outside of the microcapsule.

The outer surface of the microcapsules shell of the present invention further comprises one or more of one or more type of chemical functional groups that can then be reacted further. The surface functional groups are selected from the group consisting of —COOH, —OH, —NH$_2$, —NHR" and a protected form thereof, wherein R" is a C$_1$ to C$_7$ hydrocarbon group.

The microcapsules are prepared by interfacial polymerization. Under one embodiment of the present invention the interfacial polymerization is interfacial condensation polymerization. Under another embodiment the interfacial polymerization is interfacial addition polymerization. Under yet another embodiment the interfacial polymerization is interfacial crosslinking, wherein one of both of the reactants is a macromolecule such as a protein.

The present invention is directed to a method of preparing microcapsules comprising an active pharmaceutical ingredient, by interfacial condensation polymerization of at least two monomers, wherein at least one monomer comprises at least one surface functional selected from the group consisting of —OH, —COOH, —NH$_2$, —NHR" and a protected form thereof, wherein R" is a C$_1$ to C$_7$ hydrocarbon group, that does not react in the condensation polymerization to form a microcapsule comprising the surface functional group.

The method of preparing microcapsules according to one embodiment of the present invention comprises the steps of (a) dissolving or suspending at least one water-soluble monomer comprising at least two polymerization functional groups selected from the group consisting of hydroxyl, carboxylic acid, primary amine, secondary amine, alkene, and alkyne in a polar solvent to prepare a polar solution; (b) dissolving or suspending at least one oil-soluble monomer comprising at least two polymerization functional groups selected from the group consisting of a halide, acyl halide, sulfonyl halide, isocyanate, and isothiocyanate, and azide in a non-polar solvent to prepare a non-polar solution; wherein either the polar solution or the non-polar solution further comprises an active pharmaceutical ingredient; and wherein either the water-soluble monomer or the monomer soluble in a non-polar solvent further comprises a surface functional group selected from the group consisting of —OH, —COOH, —NH$_2$, —NHR" and protected form thereof, wherein R" is a C$_1$ to C$_7$ hydrocarbon group; and (c) contacting the polar solution with the non-polar solution to form a microcapsule comprising a core encapsulated by a shell, wherein the core comprises the active pharmaceutical ingredient and the shell comprises a polymer selected from a group consisting of polyether, polyester, polyamine, polyamide, polyurea, polyurethane, polythiocarbamate, polythiocarbonate, and triazole; and wherein the shell further comprises an outer surface of the shell, wherein the outer surface comprises a plurality of the surface functional groups.

The method of preparing microcapsules according to one embodiment of the present invention comprises at least three steps: dissolving or suspending the water-soluble monomer in a polar solvent to generate a polar solution; dissolving or suspending the oil-soluble monomer in a non-polar solvent to generate a non-polar solution; and contacting the polar solution with the non-polar solution in a way to create the microcapsule. The first step (step (a), referring to dissolving or suspending water-soluble monomer in a polar solvent), and the second step (step (b), referring dissolving or suspending oil-soluble monomer in a non-polar solvent) are meant to be carried out in any order. Under one embodiment step (a) precedes step (b). Under another embodiment step (a) follows step (b). Under another embodiment steps (a) and (b) are carried out simultaneously.

The term "dissolving" or to "dissolve" means that the solute is completely, or almost completely, dissolved within the solvent, so that the particles of the solute are not seen in the visible light wavelengths. The term "suspending" or to "suspend" or a "suspension" refers to a mixture wherein fine particles (gas, liquid or solid) as the suspension do not separate appreciably prior to the reaction of the polymeric shell.

The polar solvent and non-polar solvent are chosen so that they are not appreciably miscible with each other.

The water-soluble monomer is dissolved or suspended in a polar solvent. The polar solvent may be a polar aprotic solvent or a polar protic solvent. The polar solvent may be any of pharmaceutically acceptable polar solvent, such as water, glycerol, ethanol, and like.

Under one embodiment the polar solvent is water. The water can be of any pharmaceutical grade, and may contain any excipients or impurities, as long as the excipients or impurities do not interfere with the effective formation of the microcapsule, or otherwise interfere with other compositions in a way that would lower the drug efficacy or effectiveness. Under one embodiment the water is USP grade. Under another embodiment the water is pure water, which may be obtained by filtration, distillation, reverse osmosis, direct membrane distillation, and like.

The oil-soluble monomer is dissolved or suspended in a pharmaceutically acceptable non-polar solvent. Examples of non-polar solvents include an oil. The term "oil" includes vegetable oils, animal fats, and waxes that are of sufficient viscosity to flow at the temperatures in which the interfacial condensation polymerization takes place. Vegetable oils of the present invention are any lipid materials derived from plants, provided that the lipid material is immiscible with water, the lipid material easily dissolves, solubilizes or miscibilizes the oil-soluble monomer and the lipid material does not contain reactive chemical groups that would interfere with the interfacial condensation polymerization. Chemically, vegetable oils may be described as triglycerides. Under one embodiment of the present invention, vegetable oil contains a mixture of triglycerides, diglycerides, monoglycerides, free fatty acids and unsaponifiable lipids. Suitable vegetable oils within the scope of the present invention include edible oils, and other oils that are of plant origin. The edible oils suitable for use in the present invention include almond oil, avocado oil, canola oil, coconut oil, corn oil, cottonseed oil, diacylglycerol (DAG) oil, ghee, grape seed oil, hemp oil, lard, margarine, mustard oil, olive oil (including extra light, virgin, extra virgin, and refined), palm oil, peanut oil, groundnut oil, rapeseed oil, canola oil, rice bran oil, safflower oil, sesame oil (including semi-refined and unrefined), soybean oil, sunflower oil, sunflower oil (including high oleic, and linoleic), tea seed oil, walnut oil, and mixtures thereof. Additional oils that are suitable in the present invention include castor oil, colza oil, false flax oil, mustard oil, radish oil, ramtil oil, salicornia oil, tigernut oil, tung oil, copaiba, honge oil, jatropha oil, jojoba oil, milk bush, nahor oil, paradise oil, petroleum nut oil, dammar oil, linseed oil, flaxseed oil, poppyseed oil, stillingia oil, tung oil, vernonia oil, a mixture thereof, and a mixture with one or more edible oils.

The oil may be composed of substances that meet the ethical, cultural, dietary, or religious restrictions of the target consumer. Under one embodiment of the present invention, the oil meets the kosher standards. Under another embodiment of the present invention, the oil meets the halal standards.

The term "excipient" as used herein refers to a compound that is useful in preparing a pharmaceutical composition, generally safe, non-toxic and neither biologically nor otherwise undesirable, and includes compounds that are acceptable for human pharmaceutical use.

Either the polar solution or the non-polar solution, or both, comprises at least one surfactant. The surfactant is selected from any pharmaceutically acceptable surfactants. Exemplary surfactants include Polysorbate 20, Polysorbate 80, Tween 20, Tween 80, Macrogolglycerolhydroxystearate, Cremophor RH 40®, Triton X-100, Triton X-1000, Macrogolglycerolricinoleate, Cremophor EL®, glycerolmonooleate 40, Peceol®, Macrogolglyceryl, Labrafil M 2125 CS, propylenglycolmonolaurate FCC, Lauroglycol FCC®, Polyglycerol-6-Dioleate, propylenglycolmonocaprylate, Capryol 90®, sorbitan monolaurate, Span 20®, sorbitan monooleate, Span 80®, Vitamin E-polyethylenglycol-succinate, caprylocaproyl macrogol-8-glycerides, Labrasol®, macrogol-32-glycerol-laurate, Gelucire 44/14, glycerylmonocaprate, glycerylcaprylate, and Capmul MCM.

The contacting step follows the first two steps. The contacting step is performed in a manner that is conducive for the interfacial condensation polymerization reaction to occur. This step may be undertaken in a vessel wherein the non-polar solution and polar solution are well mixed under high sheer conditions. Such addition of energy to the mixture of the non-polar solution and polar solution aids in decreasing the microcapsule size.

The resulting mixture may contain the non-polar solution in the continuous phase and the polar solution in the discontinuous phase, simply termed, an "oil-in-water dispersion". Alternatively, the resulting mixture may contain the polar solution in the continuous phase and the non-polar solution in the discontinuous phase, or, a "water-in-oil dispersion". Thus, the prepared microcapsules may have a core that either comprises a polar solution or non-polar solution.

In addition to the above-described three-step process, the present invention is also directed to a two-step process. Under the two step process of preparing microcapsules according to another embodiment of the present invention, comprises the steps of (a) mixing of at least water, pharmaceutically acceptable oil, active pharmaceutical ingredient, a surfactant, and a water-soluble monomer comprising at least two polymerization functional groups selected from the group consisting of hydroxyl, carboxylic acid, primary amine, secondary amine, alkene, and alkyne to prepare homogeneous dispersion; and (b) adding at least one oil-soluble monomer comprising at least two polymerization functional groups selected from the group consisting of a halide, acyl halide, sulfonyl halide, isocyanate, and isothiocyanate, and azide in pharmaceutically acceptable oil to prepare an oil solution; wherein the water-soluble monomer or the oil soluble monomer or both further comprises a surface functional group selected from the group consisting —OH, —COOH, —NH$_2$, —NHR" and a protected form thereof, wherein R" is a $C_1$ to $C_7$ hydrocarbon group.

In the first step of this two-step process, all of the ingredients except the oil-soluble monomer are mixed together to create a homogeneous dispersion. In the second step the oil-soluble monomer is introduced to the dispersion. A "dispersion" is a mixture wherein one phase disperses throughout another phase.

In both the three-step and the two-step methods of preparing the microcapsule, it is useful to mix or agitate the mixture vigorously. This addition of energy to the mixture yields smaller microcapsules and uniform microcapsules.

In both of the three-step and the two-step methods of preparing the microcapsule, additional steps maybe taken. One or more steps may precede any of the steps of the three-step method. One or more steps may precede either of the steps of the two-step method. One or more steps may follow any of the steps of the three-step method. One or more steps may follow either of the steps of the two-step method.

In both of the three-step and the two-step methods of preparing the microcapsule, any of the steps may be performed at temperatures above room temperature. Elevation of the temperature may be useful in aiding the dissolution of ingredients in a solvent, aiding in mixing, increasing the reaction rates, or lowering viscosity of solutions. The temperature may be ramped during the reaction to mitigate any slowing down of the reaction associated with increasing thickness of the formed shell.

Any of the excipients, solvents, surfactants, catalysts may comply with the pharmaceutical compendial standards. Compendial standards include those listed in a reference, such as the European Pharmacopoeia, Österreichisches Arzneibuch, Farmacopéia Brasileira, Pharmacopoeia of the People's Republic of China, Český lékopis, Pharmacopoea Bohemica, The Czech Pharmacopoeia, Egyptian Pharmacopoeia, Pharmacopée française, Deutsches Arzneibuch, Deutscher Arzneimittel Codex, Neues Rezeptur Formularium, Greek Pharmacopoeia, Pharmacopoea Hungarica, Indian Pharmacopoeia, Farmakope Indonesia, Iranian Pharmacopoeia, Farmacopea Ufficiale della Repubblica Italiana, The Japanese Pharmacopoeia, The Korean Pharmacopoeia, Farmacopea de los Estados Unidos Mexicanos, Farmakopea Polska, Farmacopeia Portuguesa, Farmacopeea Romana, State Pharmacopoeia of the Russian Federation, Pharmacopoea Slovaca, Slovenský liekopis, Real Farmacopea Española, Pharmacopoea Helvetica, Thai Pharmacopoeia, The State Pharmacopoeia of the Ukraine, British Pharmacopoeia, The United States Pharmacopeia, The National Formulary, Pharmacopoeia Vietnamica, Pharmacopoea Jugoslavica, African Pharmacopoeia, and The International Pharmacopoeia.

Under interfacial condensation polymerization technique, a shell is formed on the surface of droplets (oil in water or water in oil) when water-soluble monomers react with oil-soluble monomers. It is essential that the water-soluble monomers and oil-soluble monomers are selected so that they react with each other to form a polymeric shell on the surface of the droplet. It is also important that neither the water-soluble monomer nor the oil-soluble monomer react with any of the solvents used to prepare the microcapsules, nor with the active pharmaceutical ingredient.

The water-soluble monomers comprise a plurality of polymerization functional groups. The oil-soluble monomers comprise a plurality of polymerization functional groups. The polymerization functional groups on the water-soluble monomers react with the polymerization functional groups on the oil-soluble monomers to form the polymeric shell.

The phrase "polymerization functional groups" refer to the functional groups on the monomeric compounds that react with other such groups on other monomeric compounds to form the polymeric shell. In addition to the polymerization functional groups, as described below, the monomeric compounds may also further comprise other functional groups that may further react.

Generally, the mean number of polymerization functional groups on the water-soluble monomer is 2 or more. Under one embodiment, the mean number of polymerization functional groups on the water-soluble monomer is about 2.0 to about 2.5 per water soluble monomer. Under another embodiment, the mean number of polymerization functional groups on the water-soluble monomer is about 2.3 to 2.8 per water-soluble monomer. Under still another embodiment, the mean number of polymerization functional groups on the water-soluble monomer is about 2.5 to about 3.0 per water soluble monomer.

Generally, the mean number of polymerization functional groups on the oil-soluble monomer is 2 or more. Under one embodiment, the mean number of polymerization functional groups on the oil-soluble monomer is about 2.0 to about 2.5 per oil-soluble monomer. Under another embodiment, the mean number of polymerization functional groups on the oil-soluble monomer is about 2.3 to 2.8 per oil-soluble monomer. Under still another embodiment, the mean number of polymerization functional groups on the oil-soluble monomer is about 2.5 to about 3.0 per oil-soluble monomer.

A non-integer value for the number of groups per monomer means that the monomer is a mixture of various individual molecules wherein the mean number of groups per monomer in the mixture is equal to that non-integer value.

The purpose of having more than two polymerization functional groups per molecule in either the water soluble monomers, or in the oil soluble monomers, or both, is to provide for crosslinking of the polymer chains.

One example of a combination of water-soluble monomers and oil-soluble monomers is the combination of a water-soluble compound containing —OH groups and an oil-soluble compound containing halide groups that at a high pH forms a polymer containing ether groups. The reaction of a single pair of the polymerization functional groups in this case can be represented as:

$$\text{R'—OH} + \text{R—Cl} \rightarrow \text{R'—O—R} \qquad \text{Eqn. (1)}$$

wherein R and R' each is an organic monomer; and Cl is an example of a halide.

A second example of a combination of water-soluble monomers and oil-soluble monomers is the combination of a water-soluble compound containing —COOH groups, and an oil-soluble compound containing halide groups that at a high pH forms an alkyl polymer containing ester groups. The reaction of a single pair of the polymerization functional groups in this case can be represented as:

$$\text{R'—COOH} + \text{R—Cl} \rightarrow \text{R'—C(O)—O—R} \qquad (2)$$

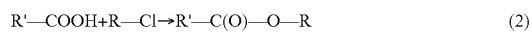

A third example of a combination of water-soluble monomers and oil-soluble monomers is the combination of a water-soluble compound containing —NH$_2$ groups, and an oil-soluble compound containing halide groups that forms a polymer containing secondary amine groups. The reaction of a single pair of the polymerization functional groups in this case can be represented as:

$$\text{R'—NH}_2 + \text{R—Cl} \rightarrow \text{R'—NH—R} \qquad (3)$$

A fourth example of a combination of water-soluble monomers and oil-soluble monomers is the combination of a water-soluble compound containing —NH— groups, and an oil-soluble compound containing halide groups that forms a polymer containing tertiary amine groups. The reaction of a single pair of the polymerization functional groups in this case can be represented as:

$$\text{R'—NH—R''} + \text{R—Cl} \rightarrow \text{R'—N(R'')—R} \qquad (4)$$

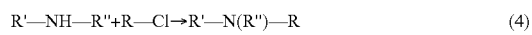

A fifth example of a combination of water-soluble monomers and oil-soluble monomers is the combination of a water-soluble compounds containing —OH groups and an oil-soluble compound containing acyl halide groups that forms a polymer containing ester groups. The reaction of a single pair of the polymerization functional groups in this case can be represented as:

$$\text{R'—OH} + \text{R—C(O)—Cl} \rightarrow \text{R—C(O)—O—R'} \qquad (5)$$

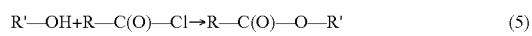

A sixth example of a combination of water-soluble monomers and oil-soluble monomers is the combination of a water-soluble compound containing —NH$_2$ groups, and an oil-soluble compound containing acyl halide groups that forms a polymer containing amide groups. The reaction of a single pair of the polymerization functional groups in this case can be represented as:

$$\text{R'—NH}_2 + \text{R—C(O)—Cl} \rightarrow \text{R—C(O)—NH—R'} \qquad (6)$$

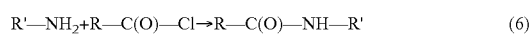

A seventh example of a combination of water-soluble monomers and oil-soluble monomers is the combination of a water-soluble compound containing —NH— groups, and an oil-soluble compound containing acyl halide groups that forms a polymer containing amide groups. The reaction of a single pair of the polymerization functional groups in this case can be represented as:

$$R'\text{—}NH\text{—}R''+R\text{—}C(O)\text{—}Cl\rightarrow R\text{—}C(O)\text{—}N(R'')\text{—}R' \tag{7}$$

An eighth example of a combination of water-soluble monomers and oil-soluble monomers is the combination of a water-soluble compound containing —OH groups, and an oil-soluble compound containing sulfonyl halide groups that forms a polymer containing esters of sulfonic acid groups. The reaction of a single pair of the polymerization functional groups in this case can be represented as:

$$R'\text{—}OH+R\text{—}SO_2Cl\rightarrow R\text{—}SO_2\text{—}O\text{—}R' \tag{8}$$

A ninth example of a combination of water-soluble monomers and oil-soluble monomers is the combination of a water-soluble compound containing —$NH_2$ groups, and an oil-soluble compound containing sulfonyl halide groups that forms a polymer containing amides of sulfonic acid groups. The reaction of a single pair of the polymerization functional groups in this case can be represented as:

$$R'\text{—}NH_2+R\text{—}SO_2Cl\rightarrow R\text{—}SO_2\text{—}NH\text{—}R' \tag{9}$$

A tenth example of a combination of water-soluble monomers and oil-soluble monomers is the combination of a water-soluble compound containing —NH— groups, and an oil-soluble compound containing sulfonyl halide groups that forms a polymer containing amides of sulfonic acid groups. The reaction of a single pair of the polymerization functional groups in this case can be represented as:

$$R'\text{—}NH\text{—}R''+R\text{—}SO_2Cl\rightarrow R\text{—}SO_2\text{—}N(R'')\text{—}R' \tag{10}$$

An eleventh example of a combination of water-soluble monomers and oil-soluble monomers is the combination of a water-soluble compound containing —OH groups, and an oil-soluble compound containing isocyanate groups that forms a polymer containing urethane groups. The reaction of a single pair of the polymerization functional groups in this case can be represented as:

$$R'\text{—}OH+R\text{—}N\!=\!C\!=\!O\rightarrow R\text{—}NH\text{—}C(O)\text{—}O\text{—}R' \tag{11}$$

A twelfth example of a combination of water-soluble monomers and oil-soluble monomers is the combination of a water-soluble compound containing —$NH_2$ groups, and an oil-soluble compound containing isocyanate groups that forms a polymer containing urea groups. The reaction of a single pair of the polymerization functional groups in this case can be represented as:

$$R'\text{—}NH_2+R\text{—}N\!=\!C\!=\!O\rightarrow R\text{—}NH\text{—}C(O)\text{—}NH\text{—}R' \tag{12}$$

A thirteenth example of a combination of water-soluble monomers and oil-soluble monomers is the combination of a water-soluble compound containing —NH— groups, and an oil-soluble compound containing isocyanate groups that forms a polymer containing urea groups. The reaction of a single pair of the polymerization functional groups in this case can be represented as:

$$R'\text{—}NH\text{—}R''+R\text{—}N\!=\!C\!=\!O\rightarrow R\text{—}NH\text{—}C(O)\text{—}N(R'')\text{—}R' \tag{13}$$

A fourteenth example of a combination of water-soluble monomers and oil-soluble monomers is the combination of a water-soluble compound containing —OH groups, and an oil-soluble compound containing isothiocyanate groups that forms a polymer containing thiocarbamate groups. The reaction of a single pair of the polymerization functional groups in this case can be represented as:

$$R'\text{—}OH+R\text{—}N\!=\!C\!=\!S\rightarrow R\text{—}NH\text{—}C(S)\text{—}O\text{—}R' \tag{14}$$

A fifteenth example of a combination of water-soluble monomers and oil-soluble monomers is the combination of a water-soluble compound containing —$NH_2$ groups, and an oil-soluble compound containing isothiocyanate groups that forms a polymer containing thiourea groups. The reaction of a single pair of the polymerization functional groups in this case can be represented as:

$$R'\text{—}NH_2+R\text{—}N\!=\!C\!=\!S\rightarrow R\text{—}NH\text{—}C(S)\text{—}NH\text{—}R' \tag{15}$$

A sixteenth example of a combination of water-soluble monomers and oil-soluble monomers is the combination of a water-soluble compound containing —NH— groups, and an oil-soluble compound containing isothiocyanate groups that forms a polymer containing thiourea groups. The reaction of a single pair of the polymerization functional groups in this case can be represented as:

$$R'\text{—}NH\text{—}R''+R\text{—}N\!=\!C\!=\!S\rightarrow R\text{—}NH\text{—}C(S)\text{—}N(R'')\text{—}R' \tag{16}$$

A seventeenth example of a combination of water-soluble monomers and oil-soluble monomers are compounds that take advantage of the click chemistry. Click chemistry (see, for example, H. C. Kolb, M. G. Finn, K. B. Sharpless, Angew. Chem., Int. Ed., 2001, 30, 2004) may be used either during the shell formation or during the surface modification. Under one embodiment, one of the monomers comprises two azide groups, and the other monomer comprises two alkyne groups, so that the azide group reacts with the alkyne group to form a triazole linking group. Huisgen cycloaddition of azides to alkynes may be used to form the microcapsule shell. Another example of the utilization of click chemistry is an addition of thiols to alkenes or alkynes including the Michael addition of thiols to α, β-unsaturated carbonyl compounds. Both types of reactions can be utilized to form shells and to modify their surface chemistry. The specific examples of the use of click chemistry to prepare microcapsules is as in FIG. 1, showing the interfacial condensation polymerization reaction between benzylic diazide and diyne deriving from a commercially available mannitol derivative.

In this seventeenth example, the linking group formed was a triazole. The term "polytriazole" is a polymer comprising triazole linking groups. Such linking groups may be formed in any manner; under one embodiment the triazole linking group is formed by a reaction of an alkyne group with an azide group.

Figure 2:
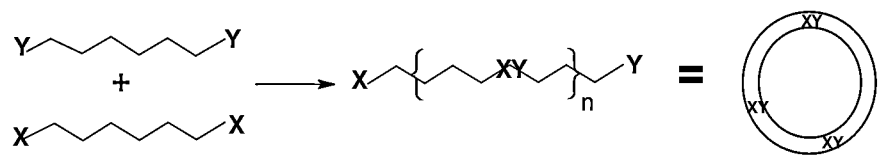
FIG. 2 is a generalized equation of the preceding seventeen equations that are a part of the present invention.

The above seventeen examples can be generalized by the following equation in FIG. 2, wherein the monomers are represented by the zigzag lines; X and Y at the end of the monomers each represent a polymerization functional group; the XY group represent a group formed from the reaction of the X polymerization functional group and Y polymerization functional group; and the annulus represents the spherical shell of the microcapsule.

The zigzag line in the equation above, and in similar the equations below, is a pictorial representation of a monomer. The zigzag line represents a monomeric compound of any structure as described herein, and does not necessarily indicate an alkyl structure, or an alkyl compound with any particular number of carbons.

The monomeric compounds that contain the above polymerization functional groups are organic compounds. Such organic compounds are generally inert with respect to the interfacial condensation polymerization, and should not negatively affect the polymerization.

The term "organic" or the phrase "organic compound" is used in its ordinary sense, which is well-known to those skilled in the art. Examples of organic compounds include hydrocarbons, that is, aliphatic (e.g., alkyl or alkenyl), alicyclic (e.g., cycloalkyl, cycloalkenyl) compounds, and aromatic-, aliphatic-, and alicyclic-substituted aromatic compounds, as well as cyclic compounds wherein the ring is completed through another portion of the molecule (e.g., two substituents together form an alicyclic compound). Further examples of organic compounds include hetero compounds, that is, compounds that contain other than carbon in a ring or chain otherwise composed of carbon atoms. Heteroatoms include sulfur, oxygen, nitrogen, and encompass compounds such as sugars, amino acids, and like. Still further examples of organic compounds include substituted hydrocarbon compounds and hetero compounds, such as compounds containing non-hydrocarbon groups, such as alkoxy, mercapto, alkylmercapto, nitro, nitroso, and sulfoxy. Yet further examples of organic compounds include macromolecules, such as proteins.

In the equation above, the monomer comprising the X groups may be a water-soluble monomer and the monomer comprising the Y groups may be an oil-soluble monomer. Alternatively, the monomer comprising the X groups may be an oil-soluble monomer and the monomer comprising the Y groups may be a water-soluble monomer.

Under one embodiment the shell of the microcapsule is formed by the reaction of at least one water-soluble monomer comprising at least two polymerization functional groups selected from the group consisting of hydroxyl, phenoxyl, carboxylic acid, primary amine, secondary amine, sulfonic acid, alkene, and alkyne; and at least one oil-soluble monomer, comprising at least two polymerization functional groups selected from the group consisting of a halide, acyl halide, sulfonyl halide, isocyanate, isothiocyanate, and azide; wherein the water-soluble monomer or the oil-soluble monomer or both, further comprises at least one surface functional group. In this case, the hydroxyl, carboxylic acid, primary amine, secondary amine, alkene, and alkyne are examples of the X group, and the halide, acyl halide, sulfonyl halide, isocyanate, isothiocyanate, and azide are examples of the Y group.

A judicious selection of the X and Y groups is crucial in order to achieve the formation of the shell, and so that neither X nor Y appreciably react with the surface functional group.

For example, the water-soluble monomer comprises at least two polymerization functional hydroxyl groups, and the oil-soluble monomer comprises at least two polymerization functional groups such as a halide, acyl halide, sulfonyl halide, isocyanate, or isothiocyanate groups. Under an embodiment in which the oil-soluble monomer comprises halide functional groups, upon reacting with the water-soluble monomer comprising hydroxyl groups, the shell formed comprises polyether. Under an embodiment in which the oil-soluble monomer comprises acyl halide functional groups, upon reacting with the water-soluble monomer comprising hydroxyl groups, the shell formed comprises polyester. Under an embodiment in which the oil-soluble monomer comprises sulfonyl halide functional groups, upon reacting with the water-soluble monomer comprising hydroxyl groups, the shell formed comprises polyesters of sulfonic acid. Under an embodiment in which the oil-soluble monomer comprises isocyanate functional groups, upon reacting with the water-soluble monomer comprising hydroxyl groups, the shell formed comprises polyurethane. Under an embodiment in which the oil-soluble monomer comprises isothiocyanate functional groups, upon reacting with the water-soluble monomer comprising hydroxyl groups, the shell formed comprises polythiocarbamate.

Alternatively, the water-soluble monomer comprises at least two polymerization functional primary amine groups, and the oil-soluble monomer comprises at least two polymerization functional groups selected from the group consisting of a halide, acyl halide, sulfonyl halide, isocyanate, and isothiocyanate. Under an embodiment in which the oil-soluble monomer comprises halide functional groups, upon reacting with the water-soluble monomer comprising primary amine groups, the shell formed comprises polyamine. Under an embodiment in which the oil-soluble monomer comprises acyl halide functional groups, upon reacting with the water-soluble monomer comprising primary amine groups, the shell formed comprises polyamide. Under an embodiment in which the oil-soluble monomer comprises sulfonyl halide functional groups, upon reacting with the water-soluble monomer comprising primary amine groups, the shell formed comprises polyamide of sulfonic acid. Under an embodiment in which the oil-soluble monomer comprises isocyanate functional groups, upon reacting with the water-soluble monomer comprising primary amine groups, the shell formed comprises polyurea. Under an embodiment in which the oil-soluble monomer comprises isothiocyanate functional groups, upon reacting with the water-soluble monomer comprising primary amine groups, the shell formed comprises polythiourea.

Alternatively, the water-soluble monomer comprises at least two polymerization functional carboxylic acid groups and the oil-soluble monomer comprises at least two polymerization functional groups selected that is a halide. The oil-soluble dihalide may be any organic dihalide that reacts with the diacid. Examples of suitable dihalides include 1,2-bis(bromomethyl)benzene, 1,3-bis(bromomethyl)benzene, 1,4-bis(bromomethyl)benzene, 1,2-bis(chloromethyl)benzene, 1,3-bis(chloromethyl)benzene, 1,4-bis(chloromethyl)benzene, and mixtures thereof.

Alternatively, the water-soluble monomer comprises at least two hydroxyl polymerization functional groups and the oil-soluble monomer comprises at least two acyl halide polymerization functional groups. Upon reaction, the shell formed comprises polyester.

Alternatively, the water-soluble monomer comprises at least two primary amine polymerization functional groups and the oil-soluble monomer comprises at least two acyl halide polymerization functional groups. Upon reaction, the shell formed comprises polyamide.

Alternatively, the water-soluble monomer comprises at least two polymerization functional groups selected from the group consisting of primary amine groups and hydroxyl groups, and the oil-soluble monomer comprises at least two sulfonyl halide polymerization functional groups. Under an embodiment in which the water-soluble monomer comprises primary amine functional groups, upon reacting with the oil-soluble monomer comprising sulfonyl halide groups, the shell formed comprises polyamides of sulfonic acid groups. Under an embodiment in which the water-soluble monomer comprises hydroxyl functional groups, upon reacting with the oil-soluble monomer comprising sulfonyl halide groups, the shell formed comprises polyester of sulfonic acid groups.

Alternatively, the water-soluble monomer comprises at least two polymerization functional groups selected from the group consisting of primary amine groups and hydroxyl groups, and the oil-soluble monomer comprises at least two isocyanate polymerization functional groups. Under an embodiment in which the water-soluble monomer comprises primary amine functional groups, upon reacting with the oil-soluble monomer comprising isocyanate groups, the shell formed comprises polyurea. Under an embodiment in which the water-soluble monomer comprises hydroxyl functional groups, upon reacting with the oil-soluble monomer comprising isocyanate groups, the shell formed comprises polyurethane.

Alternatively, the water-soluble monomer comprises at least two polymerization functional groups selected from the group consisting of primary amine groups and hydroxyl groups, and the oil-soluble monomer comprises at least two isothiocyanate polymerization functional groups. Under an embodiment in which the water-soluble monomer comprises primary amine functional groups, upon reacting with the oil-soluble monomer comprising isothiocyanate groups, the shell formed comprises polythiourea. Under an embodiment in which the water-soluble monomer comprises hydroxyl functional groups, upon reacting with the oil-soluble monomer comprising isothiocyanate groups, the shell formed comprises polythiocarbamate.

Alternatively, the water-soluble monomer comprises at least two alkyne polymerization functional groups and the oil-soluble monomer comprises at least two azide polymerization functional groups. Upon reaction, the shell formed comprises polytriazole.

In addition to water-soluble monomers comprising hydroxyl, phenoxyl, carboxylic acid, primary amine, secondary amine, sulfonic acid, alkene, or alkyne polymerization functional groups, and the oil-soluble monomers comprising halide, acyl halide, sulfonyl halide, isocyanate, isothiocyanate, thiol, or azide polymerization functional groups, the present invention is also directed to microcapsules formed by the reaction of water-soluble monomer with oil-soluble monomers, wherein the water-soluble monomers comprise halide, acyl halide, isocyanate, thiol, or azide polymerization functional groups, and the oil-soluble monomer comprise hydroxyl, phenoxyl, carboxylic acid, primary amine, secondary amine, sulfonic acid, or alkyne polymerization functional groups. Such monomers may be viewed as having "reversed solubility."

Under one embodiment the shell of the microcapsule is formed by the reaction of at least one oil-soluble monomer comprising at least two polymerization functional groups selected from the group consisting of hydroxyl, phenoxyl, carboxylic acid, primary amine, secondary amine, sulfonic acid, alkene, and alkyne; and at least one water-soluble monomer, comprising at least two polymerization functional groups selected from the group consisting of a halide, acyl halide, isocyanate, isothiocyanate, thiol and azide; wherein the water-soluble monomer or the oil-soluble monomer or both, further comprises at least one surface functional group.

For example, the oil-soluble monomer comprises at least two polymerization functional hydroxyl groups, and the water-soluble monomer comprises at least two polymerization functional groups such as a halide, acyl halide, sulfonyl halide, isocyanate, or isothiocyanate groups. Under an embodiment in which the water-soluble monomer comprises halide functional groups, upon reacting with the oil-soluble monomer comprising hydroxyl groups, the shell formed comprises polyether. Under an embodiment in which the water-soluble monomer comprises acyl halide functional groups, upon reacting with the oil-soluble monomer comprising hydroxyl groups, the shell formed comprises polyester. Under an embodiment in which the water-soluble monomer comprises sulfonyl halide functional groups, upon reacting with the oil-soluble monomer comprising hydroxyl groups, the shell formed comprises polyesters of sulfonic acid. Under an embodiment in which the water-soluble monomer comprises isocyanate functional groups, upon reacting with the oil-soluble monomer comprising hydroxyl groups, the shell formed comprises polyurethane. Under an embodiment in which the water-soluble monomer comprises isothiocyanate functional groups, upon reacting with the oil-soluble monomer comprising hydroxyl groups, the shell formed comprises polythiocarbamate.

Alternatively, the oil-soluble monomer comprises at least two polymerization functional primary amine groups, and the water-soluble monomer comprises at least two polymerization functional groups selected from the group consisting of a halide, acyl halide, and isocyanate. Under an embodiment in which the water-soluble monomer comprises halide functional groups, upon reacting with the oil-soluble monomer comprising primary amine groups, the shell formed comprises polyamine. Under an embodiment in which the water-soluble monomer comprises acyl halide functional groups, upon reacting with the oil-soluble monomer comprising primary amine groups, the shell formed comprises polyamide. Under an embodiment in which the water-soluble monomer comprises isocyanate functional groups, upon reacting with the oil-soluble monomer comprising primary amine groups, the shell formed comprises polyurea.

This type of reverse solubility can be achieved by a judicious selection or preparation of the monomers. For example, water-soluble monomer comprising at least two alkyne groups can be prepared by hydrolyzing a water-soluble dibromide followed by a reaction with propargyl bromide. Similarly, a water-soluble diolefin can be prepared by hydrolyzing a water-soluble dibromide followed by a reaction with allyl bromide.

Various monomers exhibiting the aforementioned reverse solubility may be prepared from saccharides and oligosaccharides. For example, water-soluble monomers comprising at least two isocyanate groups or two acyl halide groups, may be prepared from several oligoglycol or ionic units. Alternatively, oil-soluble monomers comprising at least two acid groups may be prepared from several oligoglycol or ionic units.

Figure 3:
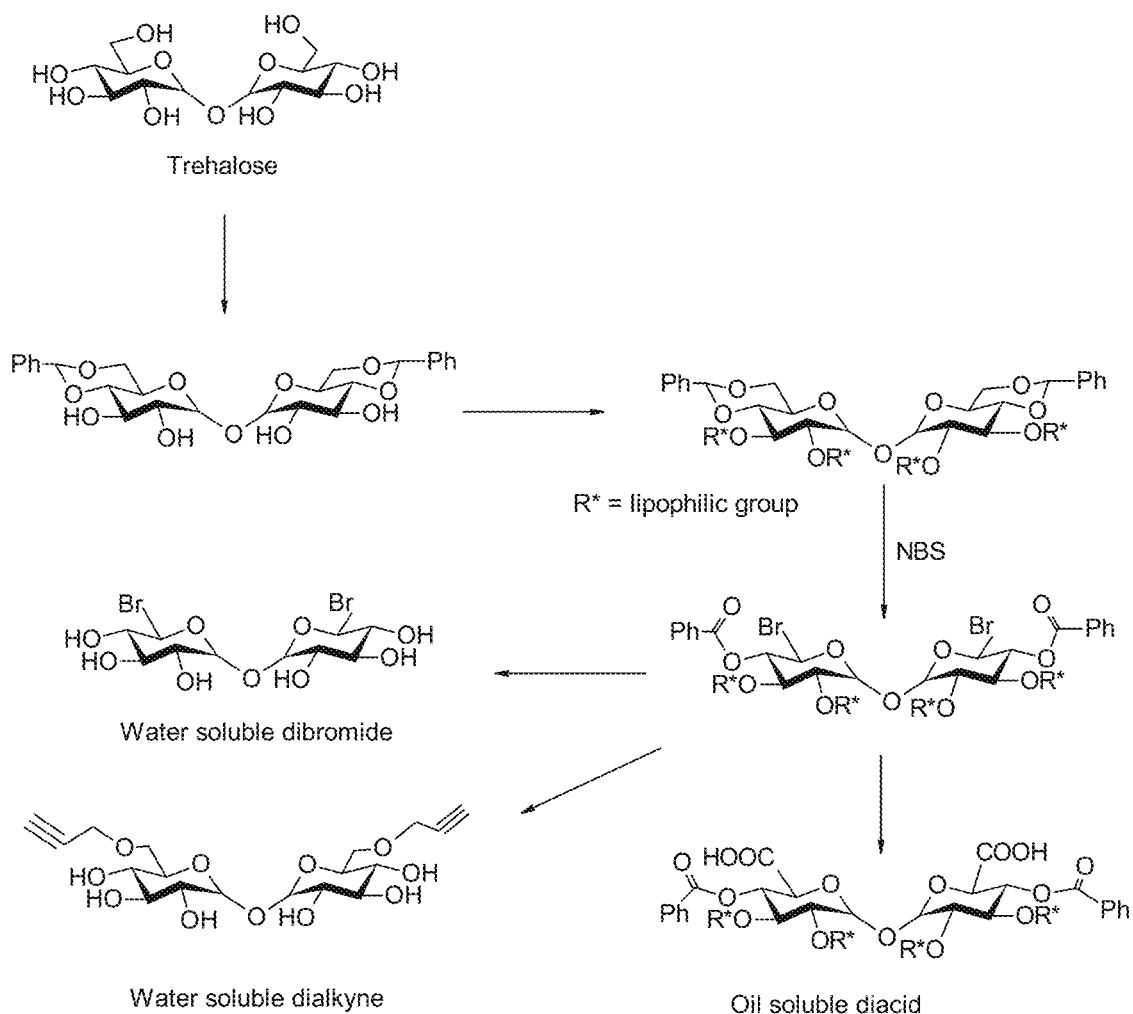
FIG. 3 is a scheme showing the preparation of a water-soluble dihalide, water-soluble dialkyne, and oil soluble diacid, which is an example of a preparation of monomers with reverse solubility.

A preparation of monomers with reverse solubility is exemplified by the scheme in FIG. 3 showing the preparation of a water-soluble dihalide, water-soluble dialkyne, and oil-soluble diacid.

The two or more polymerization functions groups on the monomer may be the same or different from each other. Under one embodiment, all polymerization functional groups on the monomer are the same. Under another embodiment, one polymerization functional group on the monomer molecule differs from another polymerization functional group.

Thus, for example, the water-soluble monomer comprises one —$NH_2$ group and at least one —OH group, and the oil-soluble monomer comprises at least two bromine groups. Upon the polymerization reaction, the microcapsule shell contains both ester linkages and amide linkages, or a copolymer of polyester and polyamide.

When referring to a polymer, the term also refers to a copolymer thereof. For example, the definition of the term "polyester" also includes copolymers of polyesters, such as polyester-polyamide copolymer.

The monomers that form the microcapsules of the present invention react with the monomers in the other phase. Under one embodiment, the monomers are stable in the solvent in which they are dissolved. For example, the water-soluble monomers are stable in the polar solvent, and the oil-soluble monomers are stable in the non-polar solvent. Under an alternative embodiment, the monomers react with the solvent, but such a reaction is slow compared to the monomer reaction with the reaction in the other phase. The monomers react preferentially with the other monomers over reaction with the solvent.

In addition to the polymerization functional groups, selected monomers involved in the formation of the shell also comprise surface functional groups. The phrase "surface functional group" is a group that is not involved in the formation of the shell of the microcapsule, but rather is a functional group that after the formation of the shell is found on the surface of the shell.

It is important that the surface functional groups be selected so that they do not interfere with the condensation reaction forming the capsules' shell. This may be done by having protecting groups present on the functional groups during the interfacial condensation polymerization, and subsequently deprotecting the functional groups.

There are various ways of forming a microcapsule comprising a shell wherein the shell comprises a surface functional group. The surface functional group may be found on one of monomers, or on the other monomer, or on both monomers. The monomers may also comprise several different surface functional groups.

Figure 4:
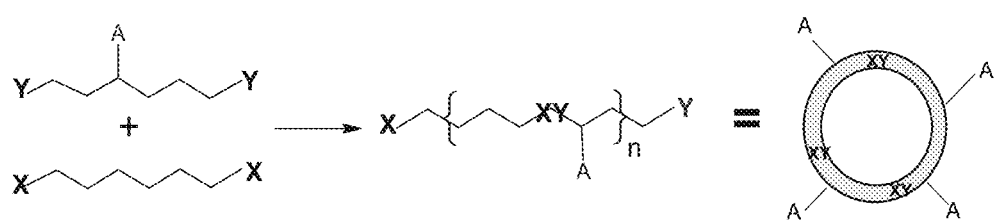
FIG. 4 is an example of forming a microcapsule comprising a shell wherein the shell comprises a surface functional group, wherein one of the monomers (either the water-soluble monomer or the oil-soluble monomer) comprises the surface functional group.

One example of forming a microcapsule comprising a shell wherein the shell comprises a surface functional group, is where one of the monomers (either the water-soluble monomer or the oil-soluble monomer) comprises the surface functional group. This example can be generalized by the equation in FIG. 4,
wherein the monomers are represented by the zigzag lines; X and Y at the end of the monomers each represent a polymerization functional group; the XY group represent a group formed from the reaction of the X polymerization functional group and Y polymerization functional group; the two short heavy parallel lines indicate that the structure on the right hand side is a formed from the pluralities of the structures in the middle of the equation; the annulus represents the spherical shell of the microcapsule; and A is a surface functional group.

Figure 5:
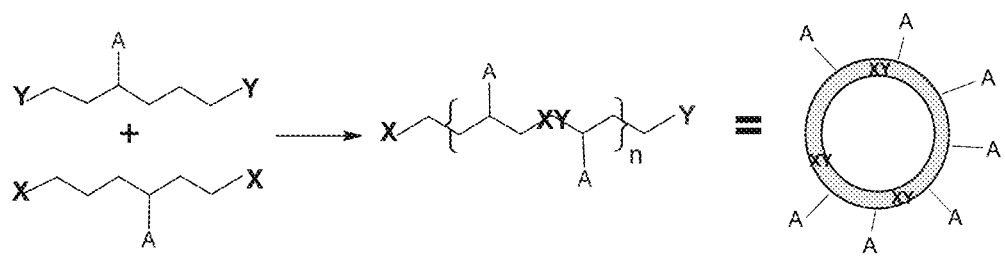
FIG. 5 is an example of forming a microcapsule comprising a shell wherein the shell comprises a surface functional group, wherein one of the monomers (either the water-soluble monomer or the oil-soluble monomer) comprises one surface functional group, and the other monomer also comprises the same functional group.

A second example of forming a microcapsule comprising a shell wherein the shell comprises a surface functional group, is where one of the monomers (either the water-soluble monomer or the oil-soluble monomer) comprises one surface functional group, and the other monomer also comprises the same functional group. This example can be generalized by the equation in FIG. 5,
wherein the symbols are as represented previously.

Figure 6:
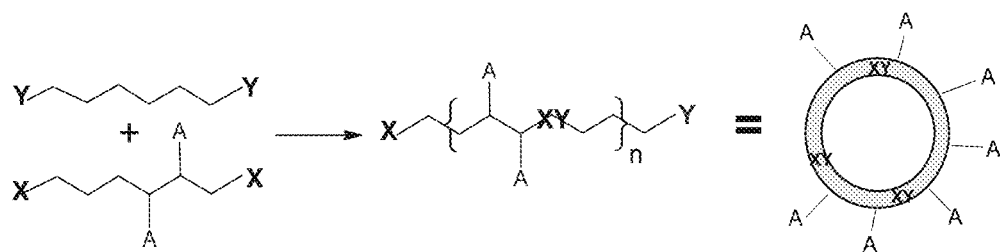
FIG. 6 is an example of forming a microcapsule comprising a shell wherein the shell comprises a surface functional group, wherein one of the monomers (either the water-soluble monomer or the oil-soluble monomer) comprises two surface functional groups.

A third example of forming a microcapsule comprising a shell wherein the shell comprises a surface functional group, is where one of the monomers (either the water-soluble monomer or the oil-soluble monomer) comprises two surface functional groups. This example can be generalized by the equation in FIG. 6,
wherein the symbols are as represented previously.

The present invention is also directed to a microcapsule comprising a shell that comprises several kinds of surface functional groups.

Figure 7:
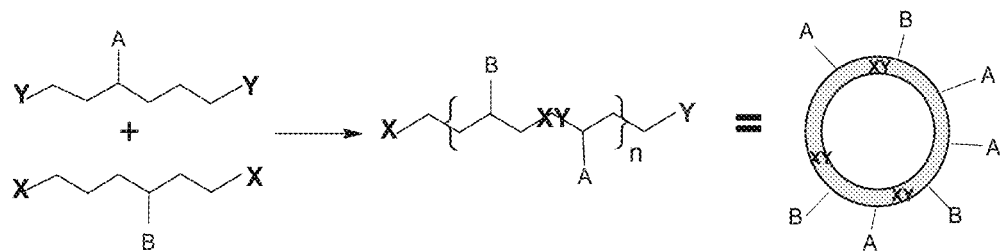
FIG. 7 is an example of forming a microcapsule comprising a shell wherein the shell comprises two types of surface functional groups, wherein one of the monomers (either the water-soluble monomer or the oil-soluble monomer) comprises one surface functional group, and the other monomer comprises a different functional group.

An example of forming a microcapsule comprising a shell wherein the shell comprises two types of surface functional groups, is where one of the monomers (either the water-soluble monomer or the oil-soluble monomer) comprises one surface functional group, and the other monomer comprises a different functional group. In this example, the surface comprises two different kinds of surface functional groups. This example can be generalized by the equation in FIG. 7,
wherein the symbols are as represented previously and wherein B is different surface functional group.

Figure 8:
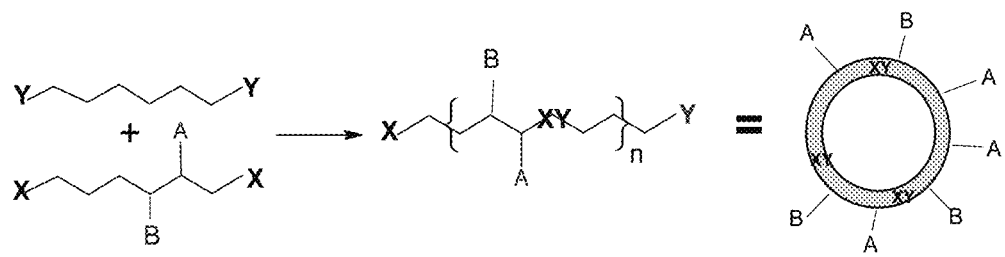
FIG. 8 is an example of forming a microcapsule comprising a shell wherein the shell comprises two different types of surface functional groups, is where one of the monomers (either the water-soluble monomer or the oil-soluble monomer) comprises two different surface functional groups.

Another example of forming a microcapsule comprising a shell wherein the shell comprises two different types of surface functional groups, is where one of the monomers (either the water-soluble monomer or the oil-soluble monomer) comprises two different surface functional groups. This example can be generalized by the equation in FIG. 8,
wherein the symbols are as represented previously.

Figure 9:
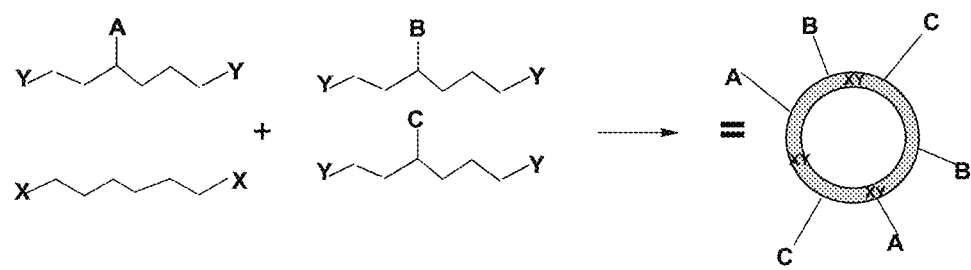
FIG. 9 is an example of forming a microcapsule comprising a shell wherein the shell comprises several different surface functional groups, achieved by using monomers (either the water-soluble monomer or the oil-soluble monomer) which comprise a mixture of two or more different monomeric compounds that contain different surface functional groups.

The preparation of microcapsules comprising a shell comprising multiple numbers of surface functional groups is also within the scope of the present invention. Because kinetics of reactions of polymerization usually do not depend on the type of the non-reactive groups present, it is possible to control the quantities of various monomers entering into the reactions of the formation of the shell. Thus, the compounds containing the same polymerization functional groups and different surface functional groups may be mixed in required proportions. Forming a microcapsule comprising a shell wherein the shell comprises several different surface functional groups, may be achieved by using one of the monomers (either the water-soluble monomer or the oil-soluble monomer) which comprise a mixture two or more different monomeric compounds that contain different surface functional groups. This example can be generalized by the equation in FIG. 9,
wherein the symbols are as represented previously, wherein A, B, and C are different surface functional group.

By the method in the previous paragraph, microcapsules comprising virtually any number of surface functional groups may be prepared. By this method it is possible to make a mixture of microcapsules with a statistical distribution of surface functional groups. Such a mixture of microcapsules may be used to investigate uptake efficacies of drugs at receptor sites that are not well understood.

Figure 10:
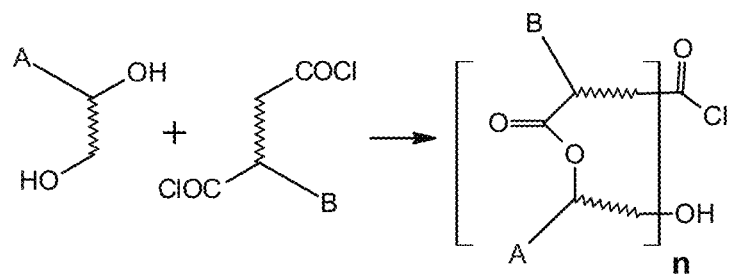
FIG. 10 is an example of a method of forming microcapsules of the present invention by formation of polyesters, wherein the water-soluble monomer comprises hydroxyl groups, and the oil-soluble monomer comprises an acyl halide groups, wherein each of the monomers may be substituted with one or more surface functional group (A and B) or other process of the polymeric shell formation.

The method of forming microcapsules of the present invention is further exemplified by the following formation of polyesters. In this example, the water-soluble monomer comprises hydroxyl groups, and the oil-soluble monomer comprises an acyl halide groups. Each of the monomers may be substituted with one or more surface functional group (A and B) or other process of the polymeric shell formation. This example can be generalized by the equation in FIG. 10, wherein the monomers are represented by the zigzag lines; —OH and —COCl at the end of the monomers are illustrative polymerization functional groups; —A and —B each represent a surface functional group.

Generally, the surface functional groups are different from either of the two polymerization functional groups present on the water-soluble and oil-soluble monomers. The surface functional group must not react with either of the two polymerization functional groups in any significant amount.

However, one of the aspects of the present invention is the placement of surface functional group on the shell that is identical to one of the polymerization functional groups. The method for preparing the microcapsules with a surface functional group that is identical to the polymerization functional group is by using a protecting group.

The protecting group is used to protect the surface functional group from reacting with any of the polymerization functional groups. The surface functional group —OH may be protected a protecting group such as acetyl, Ac, benzoyl, Bz, benzyl, Bn, β-methoxyethoxymethyl ether, MEM, methoxytrityl, (4-methoxyphenyl)diphenylmethyl, MMT, dimethoxytrityl, bis-(4-methoxyphenyl)phenylmethyl, DMT, methoxymethyl ether, MOM, p-methoxybenzyl ether, PMB, methylthiomethyl ether, pivaloyl, Piv, tetrahydropyranyl, THP, tetrahydrofuryl, THF, trityl, triphenylmethyl, Tr, silyl ether (such as trimethylsilyl, TMS, tert-butyldimethylsilyl, TBDMS, tri-iso-propyl silyloxymethyl, TOM, triisopropylsilyl, and TIPS), methyl ether, or ethoxyethyl ether.

The surface functional group —NH$_2$ may be protected by a protecting group such carbobenzyloxy, Cbz, p-methoxybenzyl carbonyl, Moz, MeOZ, tert-butyloxycarbonyl, BOC, 9-fluorenylmethyloxycarbonyl, FMOC, acetyl, Ac, benzoyl, Bz, benzyl, Bn, Carbamate, p-methoxybenzyl, PMB, 3,4-Dimethoxybenzyl, DMPM, p-methoxyphenyl, PMP, tosyl, Ts, or nosyl group.

The surface functional group —COOH may be protected by a protecting group such methyl ester, benzyl ester, tert-butyl ester, 2,6-disubstituted phenol ester (e.g. 2,6-dimethylphenol, 2,6-diisopropylphenol, 2,6-di-tert-butylphenol), silyl esters, orthoesters, or oxazoline.

The surface functional group —NR" is a secondary amine group, wherein R" is a $C_1$ to $C_7$ hydrocarbon. The phrase "$C_1$ to $C_7$ hydrocarbon" means a group consisting of hydrogen atoms and one to seven carbon atoms. The definition of the term "hydrocarbon" encompasses a saturated hydrocarbon group, an unsaturated hydrocarbon group, an aliphatic group, or an aromatic group, and a mixture thereof. Examples of hydrocarbon group includes alkyl, alkenyl, alkynyl, aryl, and a mixture thereof.

Examples of a $C_1$ to $C_7$ hydrocarbon include $C_1$ to $C_7$ alkyl groups. Such alkyl groups may be straight or substituted. Examples of $C_1$ to $C_7$ alkyl groups include $CH_3$, $C_2H_5$, $C_3H_7$, $C_4H_9$, $C_5H_{11}$, $C_6H_{13}$, $C_7H_{15}$, methyl, ethyl, propyl, n-propyl, isopropyl, butyl, n-butyl, iso-butyl, sec-butyl, pentyl, n-pentyl, 1-methylbutyl, 2-methylbutyl, 3-methylbutyl, hexyl, n-hexyl, 1-methylpentyl, 2-methylpentyl, 3-methylpentyl, 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,1,2-trimethylpropyl; 1-ethyl-1-methylpropyl; 1-ethyl-2-methylpropyl; heptyl; n-heptyl, 1-methylhexyl; 2-methylhexyl; 3-methylhexyl; 4-methylhexyl; 5-methylhexyl; 1,1-dimethylpentyl; 1,2-dimethylpentyl; 1,3-dimethylpentyl; 1,4-dimethylpentyl; 2,2-dimethylpentyl; 2,3-dimethylpentyl; 2,4-dimethylpentyl; 3,3-dimethylpentyl; 3,4-dimethylpentyl; 4,4-dimethylpentyl; 1-ethylpentyl; 2-ethylpentyl; 3-ethylpentyl; 1,1,2-trimethylbutyl; 1, 1,3-trimethylbutyl; 1,2,2-trimethylbutyl; 1,2,3-trimethylbutyl; 1,3,3-trimethylbutyl; 2,2,3-trimethylbutyl; 2,3,3-trimethylbutyl; 1-ethyl-1-methylbutyl; 1-ethyl-2-methylbutyl; 1-ethyl-3-methylbutyl; 2-ethyl-1-methylbutyl; 2-ethyl-2-methylbutyl; 2-ethyl-3-methylbutyl; 1-propylbutyl; 1-isopropylbutyl; 1,1,2,2-tetramethylpropyl; 1-ethyl-1,2-dimethylpropyl; 1-ethyl-2,2-dimethylpropyl; and 1,1-diethylpropyl.

Examples of a $C_1$ to $C_7$ hydrocarbon further include $C_2H_3$, $C_3H_5$, $C_4H_7$, $C_5H_9$, $C_6H_{11}$, $C_7H_{13}$, $C_2H$, $C_3H_3$, $C_4H_5$, $C_5H_7$, $C_6H_9$, $C_7H_{11}$; $C_3H$, $C_4H_3$, $C_5H_5$, $C_6H_7$, $C_7H_9$; $C_4H$, $C_5H_3$, $C_6H_5$, $C_7H_7$.

Examples of $C_1$ to $C_7$ hydrocarbon still further include cyclic groups, such as cyclopropyl, cyclobutyl, cyclopentyl, cyclohexyl, and cycloheptyl.

Examples of $C_1$ to $C_7$ hydrocarbon also include aryl groups, such as benzyl, o-tolyl, m-tolyl, and p-tolyl.

The $C_1$ to $C_7$ hydrocarbon group R" in the secondary amine —NR" is chosen such that the reactivity of the amine group with the reactant RZ is controlled, taking into account the identities and reactivities of the aforementioned X group, Y group, Z group, steric effects and electronic effects of the R" group, and like.

As a way of example for preparation of microcapsules wherein the microcapsule comprises surface functional groups that are identical the polymerization functional groups, a glycerol wherein the secondary —OH group is protected, is reacted with a monomer comprising acyl halide groups. After interfacial condensation polymerization, the protected —OH groups is present on the surface of capsules. A subsequent deprotection step of the —OH group produces microcapsules with reactive hydroxyl groups on the surface. It is important that the deprotection step that does not affect the ester functionality forming the structure of the shell.

Examples of monomers comprising two hydroxyl groups (diols) that are useful in preparation of microcapsules of the present invention include oligomers of ethylene and propylene glycols, glycerol, butanediol, hexanediol, dihydroxybenzene, benzenediol, and dihydroxymethylbenzene. Additional examples include monosaccharides, oligosaccharides, polysaccharides. Monosaccharides and oligosaccharides are exceptionally attractive diols, since there is a plethora of carbohydrate scaffolds containing various protected functional groups, and additional non-protected, reactive hydroxyl groups.

Examples of monomers comprising carboxylic acid groups include terephthalic acid, isophthalic acid, phthalic acid, maleic and fumaric acids, malonic acid, oxalic acid, and citric acid. Additional example include dicarboxylic acids derived from carbohydrates.

Examples of diamino compounds include some amino acids, proteins and peptides.

The number of surface functional groups on the surface of a microcapsule may be controlled by adding of monomers that do not comprise any surface functional groups.

The microcapsule as described above contains at least one surface functional groups selected from the group consisting of —OH, —COOH, —NH$_2$, —NHR" and a protected form thereof, wherein R" is a $C_1$ to $C_7$ hydrocarbon group. Under one embodiment, the microcapsule may be isolated, and formulated into a medical composition. Under another embodiment, the microcapsule may be reacted further with a reactant, so that the reactant may be grafted onto the surface of the microcapsule via the surface functional group.

The present invention is also directed to a method of modifying the microcapsules comprising surface functional groups by performing reactions with the surface functional groups. In such a way, different groups may be grafted onto the surface of the microcapsule.

The present invention is also directed to a grafted microcapsule. A grafted microcapsule comprises a reaction product of the microcapsule described above, and a reactant of formula RZ, wherein Z is selected from a group consisting of halide, acyl halide, sulfonyl halide, anhydride, azide, thio, isocyanate, and isothiocyanate; and R is an organic group selected from the group consisting of a hydrophilic group, a thiosugar, a monosaccharide, an oligosaccharide, a polysaccharide, a protein, and a hydrophobic group.

Figure 11:
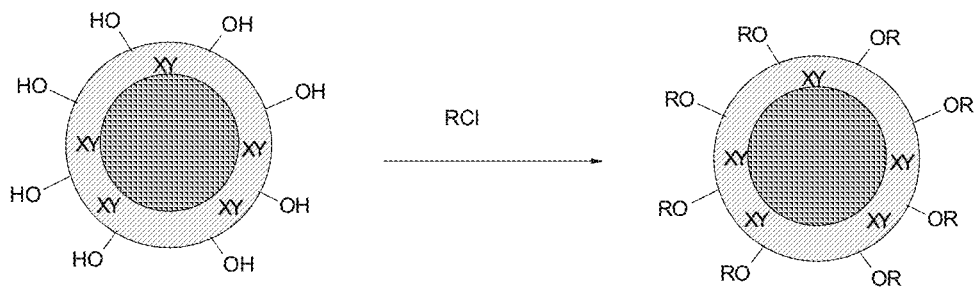
FIG. 11 is an example of the surface functional groups being reacted with a reactant, in which the reactant residue is grafted onto the surface of the microcapsule.

The surface functional groups are reacted with a reactant, in which the reactant residue is grafted onto the surface of the microcapsule. This may be illustrated as in FIG. 11, wherein —OH is a hydroxyl group exemplifying a surface functional group; RCl is an organic chloride that exemplifies a reactant that can be grafted onto the surface of the microcapsule through an ether bond. The R is the reactant residue of the reactant RCl, or "graft".

A "graft", as used herein, is the residue of a reactant that has been bonded onto the surface of the microcapsule. A "grafted microcapsule" is a microcapsule that comprises at least one graft.

The residue (exemplified as R in FIG. 11)) is an organic group selected from the group consisting of a hydrophilic group, a thiosugar, a monosaccharide, an oligosaccharide, a polysaccharide, a protein, and a hydrophobic group.

The selection of the surface functional groups, and the grafts have a great impact on the physical and chemical properties of the microcapsules, and thus on the efficacy of the drug. The transport properties of microcapsules are affected by the hydrophilicity of the microcapsules. The hydrophilicity of microcapsules can be increased by increasing the number of hydrophilic groups on the surface of the microsphere. Such hydrophilic groups include hydroxyl, carboxylic acid, and sulfonic acid groups. Such hydrophilic groups may be either a surface functional group (i.e., they were present on the monomer), or they may be present on the graft. Nonionic moieties, like those of polyethylene glycol, polypropylene glycol or those deriving from protected carbohydrates can be used.

Alternatively, if the microcapsule is used in an oil medium, then the surface of the microcapsule should have hydrophobic groups. This may be achieved by grafting long hydrocarbon chains onto the surface.

In some applications of the present invention, it may be beneficial to introduce the active pharmaceutical ingredient by multiple means that may require a series of different surface groups. A mixture of microcapsules may be introduced to the patient.

The presence of residue may perform one or more of various functions. Under one example, the residue facilitates the transport of the microcapsule to the desired location. Under another example, the residue facilitates in arresting the microcapsules at the desired location.

The presence of a hydrophilic group on the surface of a microcapsule makes the surface of the microcapsule hydrophilic and such hydrophilicity makes it easy to travel in an aqueous environment such as GI tract, blood, and spinal fluid. Examples of a hydrophilic group include —COOH, —OH, —$SO_2OH$, —$NH_2$, and salts thereof The residue may also be selected to ease the crossing of various barriers in the human body. Under one embodiment the residue is a thiosugar residue, which may be used to allow for crossing of the blood-brain barrier by the grafted microcapsule. A thiosugar is a sugar analog in which any one of the oxygen atoms is replaced by a sulfur atom. For example, a sulfur atom may replace the ring oxygen. A thiosugar contains a sulfur atom as a heteroatom or is a disaccharide linked via a sulfur bridge. Examples of thiosugars which are suitable for grafting onto the surface of the microcapsule include 1,4-thioanhydrosugars, 1,6-thioanhydrosugars, tagetioxin, thiolactomycin, and analogues thereof A plurality of residues may be present on the surface of a microcapsule. The selection of various residues, at various ratios or concentrations may be employed to obtain a desired hydrophilic/hydrophobic balance. The choice of a proper hydrophilic/hydrophobic balance may be necessary to facilitate a transport of the microcapsules through various bodily membranes.

Under another embodiment, the residue is used to prevent agglomeration of microcapsules. Examples of such residues are those that have properties similar to non-ionic surfactants. These may include a mixture of hydrophobic and hydrophilic groups.

The residues may also function as an aid in arresting the capsules at the desired location in the human body. For example, a protein residue may be recognized by receptors on the surface of a cell.

Monosaccharides, disaccharides, oligosaccharide, and polysaccharides may also be used for the same purpose. Monosaccharides include aldotrioses, aldotetroses, aldopentoses, aldohexoses, ketotrioses, ketotetroses, ketopentoses, and ketohexoses. Examples of such monosaccharides include glyceraldehyde, erythrosine, throes, ribose, arabinose, xylose, xylose, aloes, altos, glucose, mannose, glucose, diose, galactose, talose, glycorone, erythrulose, ribulose, xylulose, psicose, fructose, sorbose, and tagatose. Under one embodiment the residue is selected from the group consisting of galactose and manose.

It is also possible to have several different groups grafted onto the surface of the microcapsule. The surface functional groups are reacted with various reactants that are added to the reaction mixture. Under one embodiment, these reactants are added simultaneously in desired proportions. This may be illustrated by the following reaction scheme in FIG. 12, wherein OH is a hydroxyl group exemplifying a surface functional group; mol. is molar equivalents of reactants to the moles of surface functional groups; $R_1$ Cl, $R_2$Cl, $R_3$Cl, and $R_4$Cl are alkyl halides that exemplify reactive compounds that can be grafted onto the surface of the microcapsule through an ether bond.

These reactions of microcapsules with a mixture of reactive species can take place concurrently, or serially, or a mixture thereof. For example, referring to the exemplary reaction scheme in FIG. 12, Reactive Compound Rid is added first, and the reaction of $R_1$Cl with a portion of the surface functional groups is carried out to completion. Reactive Compound $R_2$Cl is added next, and the reaction of $R_2$Cl with a portion of the surface functional groups is carried out to completion. Then Reactive Compound $R_3$Cl is added, and the reaction of $R_3$Cl with a portion of the surface functional groups is carried out to completion. Finally, Reactive Compound $R_4$Cl is added, and the reaction of $R_4$Cl with a portion of the surface functional groups is carried out to completion.

Figure 12:
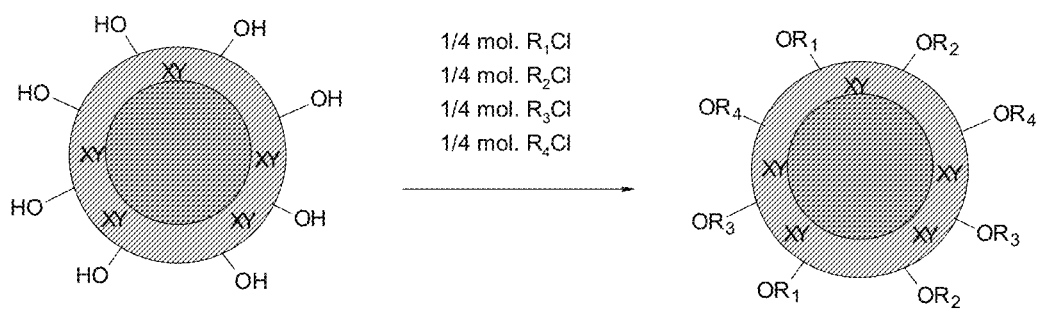
FIG. 12 is an example surface functional groups being reacted with various reactants that are added to the reaction mixture resulting in a microcapsule that has several different groups grafted onto its surface.

In a different example of the exemplary reaction scheme in FIG. 12 a mixture of $R_1$Cl, $R_2$Cl, $R_3$Cl, and $R_4$Cl are added to the solution comprising the microcapsules simultaneously.

In a still different example of the exemplary reaction scheme in FIG. 12, Reactive Compound $R_1$Cl is added first, and the reaction of $R_1$Cl with a portion of the surface functional groups is carried out to completion. Then a mixture of Reactive Compounds $R_2$Cl, and $R_3$Cl is added next, and the reaction of $R_2$Cl and $R_3$Cl with a portion of the surface functional groups is carried out to completion. Finally, Reactive Compound $R_4$Cl is added, and the reaction of $R_4$Cl with a portion of the surface functional groups is carried out to completion.

The present invention also allows to selectively react the surface functional group with reactants. Under one embodiment, the microcapsule comprises surface functional groups wherein a limited number of surface functional groups ("minor groups") are different from the grafted surface functional groups ("major groups") on the microcapsule. This is achieved in several steps. In the first step, the microcapsules are formed with only the major surface functional groups. In the second step, selected surface functional groups are reacted with an appropriately functionalized substrate. The microcapsule adheres onto the substrate via bonds to minor amount of the surface functional groups. In the third step, all the surface functional groups that are not reacted with the substrate are reacted further. In the fourth step, the microcapsule is decoupled from the flat surface to produce a capsules comprising minor surface functional groups and major surface functional groups. An example of a suitable substrate includes the surface of mica (a composition that is known to be equipped with —OH groups, and that has been treated in a way that it reacts with the surface functional groups on the microcapsules. This example can be generalized by the equation in FIG. 13.
wherein X is a functional group on the substrate, OH is hydroxyl group on the microcapsule, RY is a reactant (such as an alkyl halide) that reacts with OH on the microcapsule to form —OR ether groups on the microcapsule.

Figure 13:
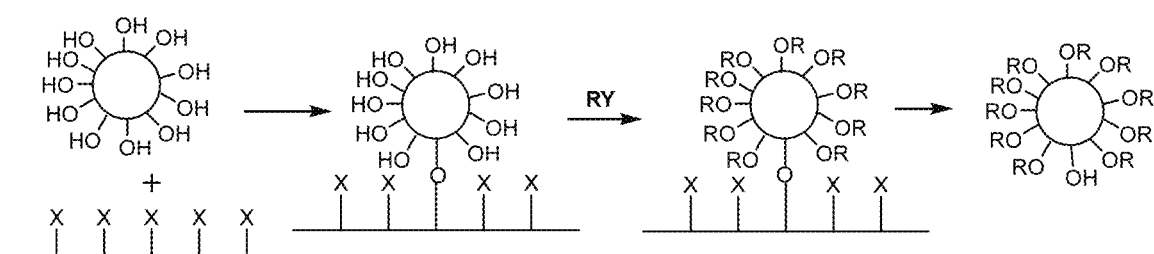
FIG. 13 is an example of selectively reacting the surface functional groups with reactants. Here, the microcapsule comprises surface functional groups wherein a limited number of surface functional groups ("minor groups") are different from the grafted surface functional groups ("major groups") on the microcapsule. In the first step, the microcapsules are formed with only the major surface functional groups. In the second step, selected surface functional groups are reacted with an appropriately functionalized substrate. The microcapsule adheres onto the substrate via bonds to minor amount of the surface functional groups. In the third step, all the surface functional groups that are not reacted with the substrate are reacted further. In the fourth step, the microcapsule is decoupled from the flat surface to produce a capsule comprising minor surface functional groups and major surface functional groups.

The minor groups, illustrated by as OH in the schematic equation in FIG. 13, may be reacted further to graft a residue that is much different from the other major groups.

In the above schematic equation in FIG. 13 the resulting microcapsule is shown only with a single OH group, it is recognized that the microcapsule may have any number of minor surface functional groups. Under one embodiment the ratio of the major groups to the minor groups (illustrated as OR and OH in schematic equation in FIG. 13, respectively) is <2:1. Such microcapsule may be characterized as a Janus particle, wherein one hemisphere of the microsphere is mostly hydrophobic, and the other hemisphere is mostly hydrophilic. The use of Janus microcapsule allows for better positioning of the microcapsule within the patient's body. Such microcapsules may also act as a surfactant.

Another example of a method of modifying the microcapsules comprising surface functional groups by performing reactions with the surface functional groups is the use of bio-orthogonal reactions (i.e., reactions that do not interfere with biological processes; see E. M. Sletten, C. R. Bertozzi, *Angew. Chem. Int. Ed.* 2009, 49, 6974; M. Boyce, C. R. Bertozzi, *Nat. Methods,* 2011, 8, 638).

Further example of biologically friendly surface functional groups are carbohydrates. Microcapsules may be functionalized with neoglyco-conjugates of biologically significant oligosaccharides, in a similar way as for glyconanoparticles. See M. Marradi, M. Martin-Lomas, S. Penades, *Adv. Carbohydr. Chem. Biochem.* 2013, 42(11) 4728-4745; D. C. Kennedy, D. Grünstein, C. H. Lai, P. H. Seeberger, *Chem. Eur. J.* 2013, 19, 3974-3800.

The present invention is also directed to a medical composition comprising the microcapsule. The medical composition is used to administer the active pharmaceutical ingredient to a patient in need of the active pharmaceutical ingredient.

The present invention is also directed to a medical composition comprising the grafted microcapsule. The medical composition comprising grafted microcapsules is used to administer the active pharmaceutical ingredient to a patient in need of the active pharmaceutical ingredient.

The medical composition comprising the microcapsule, or the grafted microcapsule, can be administered in any of the typical routes of administration, including enteral, parenteral, oral, intravenous, rectal, topical, sublingual, subcutaneous, or by inhalation.

The form of the medical composition is dependent on the route of administration. For example, a polar formulation may be used for oral, intravenous, subcutaneous or topical delivery. A solid formulation may be used for rectal or sublingual administration.

A medical composition for oral administration route generally requires an aqueous composition wherein the microcapsule mixed and suspended within the aqueous composition. Alternatively, the microcapsule may be mixed with pharmaceutically acceptable oil and administered.

An aqueous form of the medical composition comprising the microcapsules of the present invention may optionally comprise anticoagulants. Anticoagulants may be used to mitigate clumping of microcapsules, which may be present due to the surface properties of the microcapsules.

Under one embodiment of the present invention, the release of active pharmaceutical ingredient from the microcapsule of the present invention is similar to the release of active pharmaceutical ingredient from microcapsules as known in the art. One form of such release is a controlled release over time. Such a release may be a slow diffusion of the active pharmaceutical ingredient through the shell. Another form of release is by rupturing of the shell and disgorging the contents of the core including the active pharmaceutical ingredient. The release of the active pharmaceutical ingredient from the capsule might be triggered by a pH change, or presence of certain enzymes at the location.

Triggering of release by enzymes may be accomplished by the enzymes breaking bonds within the shell. For example, such enzymes may hydrolyze the ester or amide bonds of the polyester or polyamide polymer of the shell. Under one embodiment, such enzymes are present at the location of interest. Under another embodiment, such enzymes are introduced into the location of interest after the delivery of the microcapsule. Under still another embodiment, the enzymes are microencapsulated.

Under another embodiment, the microcapsules of the present invention are equipped with functionalities that are recognized by receptors present only on the surface of a target organ, so that the microcapsules end up near the target organ. The release takes place after the capsules reached the required destination.

Under another embodiment, ultrasound is used to rupture the shell to release the active pharmaceutical ingredient from the microcapsule. The ultrasound may be administered externally directly, or indirectly; it may be reflected or focused (see, D. Lenses, et al. *Soft Matter, Royal Society of Chemistry,* 2011, 7, 5417-5422). Under another embodiment the ultra sound of two different frequencies may be used to selectively rupture two different types of microcapsules.

Under still another embodiment, the microcapsule comprises ferromagnets. Such magnets may be located within the core of the microcapsule, or in the shell. Such use of ferromagnets may be useful aiding targeting of the microcapsules, or alternatively, in releasing of the active pharmaceutical ingredient from the microcapsule.

Under yet another embodiment of the present invention, there is no rupture of the shell after the delivery of the microcapsule to the desired location. Under this embodiment, the functional groups or grafted groups on the surface help with the delivery of the microcapsule to the desired location where the specific receptors couple with corresponding functional groups on the surface of capsules, as in some of the previously recited embodiments, except that the contents in the core of the microcapsules are not released into the body, but instead remain within the microcapsules.

One example of the use of microcapsules that do not release its cargo is radiotherapeutic compounds, or other diagnostic compounds. Another example of the use of microcapsules that do not release its cargo is neutron capture therapy, wherein the microcapsules are able to deliver to a cancer cell much greater amount of alpha particle releasing atoms than would a delivery without the microencapsulation.

The microcapsules of the present invention are applicable to the delivery of active pharmaceutical ingredient targeting various diseases. However, the microcapsules are particularly suited for drugs that are expected to address diseases of single organs. The microcapsules are also particularly suited for drugs that are to act in a well-defined location within the body such as a particular organ. The microcapsules are well suited to the delivery of drugs acting on various cancers of a single organ, such as lung cancer or kidney cancer. The microcapsules are suitable for delivery of active pharmaceutical ingredient to treat tuberculosis, lung disease, kidney disease, throat disease, and pancreas diseases. The microcapsules of the present invention are applicable for delivery of painkillers.

However, the identity of active pharmaceutical ingredients that may be delivered by the microcapsules of the present invention is not limited. Additional examples of active pharmaceutical ingredients that may be delivered by the microcapsules include active pharmaceutical ingredient of one or more of the following classes: (1) Adrenergic agonists such as, for example, amphetamine, apraclonidine, bitolterol, clonidine, colterol, dobutamine, dopamine, ephedrine, epinephrine, ethylnorepinephrine, fenoterol, formoterol, guanabenz, guanfacine, hydroxyamphetamine, isoetharine, isoproterenol, isotharine, mephenterine, metaraminol, methamphetamine, methoxamine, methpentermine, methyldopa, methylphenidate, metaproterenol, metaraminol, mitodrine, naphazoline, norepinephrine, oxymetazoline, pemoline, phenylephrine, phenylethylamine, phenylpropanolamine, pirbuterol, prenalterol, procaterol, propylhexedrine, pseudoephedrine, ritodrine, salbutamol, salmeterol, terbutaline, tetrahydrozoline, tramazoline, tyramine and xylometazoline; (2) adrenergic antagonists such as, for example, acebutolol, alfuzosin, atenolol, betaxolol, bisoprolol, bopindolol, bucindolol, bunazosin, butyrophenones, carteolol, carvedilol, celiprolol, chlorpromazine, doxazosin, ergot alkaloids, esmolol, haloperidol, indoramin, ketanserin, labetalol, levobunolol, medroxalol, metipranolol, metoprolol, nebivolol, nadolol, naftopidil, oxprenolol, penbutolol, phenothiazines, phenoxybenzamine, phentolamine, pindolol, prazosin, propafenone, propranolol, sotalol, tamsulosin, terazosin, timolol, tolazoline, trimazosin, urapidil and yohimbine, (3) adrenergic neurone blockers such as, for example, bethanidine, debrisoquine, guabenxan, guanadrel, guanazodine, guanethidine, guanoclor and guanoxan; (4) drugs for treatment of addiction, such as, for example, buprenorphine; (5) drugs for treatment of alcoholism, such as, for example, disulfuram, naloxone and naltrexone; (6) drugs for Alzheimer's disease management, including acetylcholinesterase inhibitors such as, for example, donepezil, galantamine, rivastigmine and tacrin; (7) anaesthetics such as, for example amethocaine, benzocaine, bupivacaine, hydrocortisone, ketamine, lignocaine, methylprednisolone, prilocalne, proxymetacaine, ropivacaine and tyrothricin; (8) angiotensin converting enzyme inhibitors such as, for example, captopril, cilazapril, enalapril, fosinopril, imidapril hydrochloride, lisinopril, moexipril hydrochloride, perindopril, quinapril, ramipril and trandolapril; (9) angiotensin II receptor blockers, such as, for example, candesartan, cilexetil, eprosartan, irbesartan, losartan, medoxomil, olmesartan, telmisartan and valsartan; (10) antiarrhythmics such as, for example, adenosine, amidodarone, disopyramide, flecamide acetate, lidocaine hydrochloride, mexiletine, procainamide, propafenone and quinidine; 11) Antibiotic and antibacterial agents (including the beta-lactams, fluoroquinolones, ketolides, macrolides, sulphonamides and tetracyclines) such as, for example, aclarubicin, amoxicillin, amphotericin, azithromycin, aztreonam chlorhexidine, clarithromycin, clindamycin, colistimethate, dactinomycin, dirithromycin, doripenem, erythromycin, fusafungine, gentamycin, metronidazole, mupirocin, natamycin, neomycin, nystatin, oleandomycin, pentamidine, pimaricin, probenecid, roxithromycin, sulphadiazine and triclosan; (12) anticlotting agents such as, for example, abciximab, acenocoumarol, alteplase, aspirin, bemiparin, bivalirudin, certoparin, clopidogrel, dalteparin, danaparoid, dipyridamole, enoxaparin, epoprostenol, eptifibatide, fondaparin, heparin (including low molecular weight heparin), heparin calcium, lepirudin, phenindione, reteplase, streptokinase, tenecteplase, tinzaparin, tirofiban and warfarin; (13) anticonvulsants such as, for example, GABA analogs including tiagabine and vigabatrin; barbiturates including pentobarbital; benzodiazepines including alprazolam, chlordiazepoxide, clobazam, clonazepam, diazepam, flurazepam, lorazepam, midazolam, oxazepam and zolazepam; hydantoins including phenyloin; phenyltriazines including lamotrigine; and miscellaneous anticonvulsants including acetazolamide, carbamazepine, ethosuximide, fosphenyloin, gabapentin, levetiracetam, oxcarbazepine, piracetam, pregabalin, primidone, sodium valproate, topiramate, valproic acid and zonisamide; (14) antidepressants such as, for example, tricyclic and tetracyclic antidepressants including amineptine, amitriptyline (tricyclic and tetracyclic amitryptiline), amoxapine, butriptyline, cianopramine, clomipramine, demexiptiline, desipramine, dibenzepin, dimetacrine, dosulepin, dothiepin, doxepin, imipramine, iprindole, levoprotiline, lofepramine, maprotiline, melitracen, metapramine, mianserin, mirtazapine, nortryptiline, opipramol, propizepine, protriptyline, quinupramine, setiptiline, tianeptine and trimipramine; selective serotonin and noradrenaline reuptake inhibitors (SNRIs) including clovoxamine, duloxetine, milnacipran and venlafaxine; selective serotonin reuptake inhibitors (SSRIs) including citalopram, escitalopram, femoxetine, fluoxetine, fluvoxamine, ifoxetine, milnacipran, nomifensine, oxaprotiline, paroxetine, sertraline, sibutramine, venlafaxine, viqualine and zimeldine; selective noradrenaline reuptake inhibitors (NARIS) including demexiptiline, desipramine, oxaprotiline and reboxetine; noradrenaline and selective serotonin reuptake inhibitors (NASSAs) including mirtazapine; monoamine oxidase inhibitors (MAOIs) including amiflamine, brofaromine, clorgyline, a-ethyltryptamine, etoperidone, iproclozide, iproniazid, isocarboxazid, mebanazine, medifoxamine, moclobemide, nialamide, pargyline, phenelzine, pheniprazine, pirlindole, procarbazine, rasagiline, safrazine, selegiline, toloxatone and tranylcypromine; muscarinic antagonists including benactyzine and dibenzepin; azaspirones including buspirone, gepirone, ipsapirone, tandospirone and tiaspirone; and other antidepressants including acetaphenazine, ademetionine, S-adenosylmethionine, adrafinil, amesergide, amineptine, amperozide, benactyzine, benmoxine, binedaline, bupropion, carbamazepine, caroxazone, cericlamine, cotinine, fezolamine, flupentixol, idazoxan, kitanserin, levoprotiline, lithium salts, maprotiline, medifoxamine, methylphenidate, metralindole, minaprine, nefazodone, nisoxetine, nomifensine, oxaflozane, oxitriptan, phenyhydrazine, rolipram, roxindole, sibutramine, teniloxazine, tianeptine, tofenacin, trazadone, tryptophan, viloxazine and zalospirone; (15) anticholinergic agents such as, for example, atropine, benzatropine, biperiden, cyclopentolate, glycopyrrolate, hyoscine, ipratropium bromide, orphenadine hydrochloride, oxitroprium bromide, oxybutinin, pirenzepine, procyclidine, propantheline, propiverine, telenzepine, tiotropium, trihexyphenidyl, tropicamide and trospium; (16) antidiabetic agents such as, for example, pioglitazone, rosiglitazone and troglitazone; (17) antidotes such as, for example, deferoxamine, edrophonium chloride, fiumazenil, nalmefene, naloxone, and naltrexone; (18) antiemetics such as, for example, alizapride, azasetron, benzquinamide, bestahistine, bromopride, buclizine, chlorpromazine, cinnarizine, clebopride, cyclizine, dimenhydrinate, diphenhydramine, diphenidol, domperidone, dolasetron, dronabinol, droperidol, granisetron, hyoscine, lorazepam, metoclopramide, metopimazine, nabilone, ondansetron, palonosetron, perphenazine, prochlorperazine, promethazine, scopolamine, triethylperazine, trifluoperazine, triflupromazine, trimethobenzamide and tropisetron; (19) antihistamines such as, for example, acrivastine, astemizole, azatadine, azelastine, brompheniramine, carbinoxamine, cetirizine, chlorpheniramine, cinnarizine, clemastine, cyclizine, cyproheptadine, desloratadine, dexmedetomidine, diphenhydramine, doxylamine, fexofenadine, hydroxyzine, ketotifen, levocabastine, loratadine, mizolastine, promethazine, pyrilamine, terfenadine and trimeprazine; (20) anti-infective agents such as, for example, antivirals (including nucleoside and non-nucleoside reverse transcriptase inhibitors and protease inhibitors) including aciclovir, adefovir, amantadine, cidofovir, efavirenz, famiciclovir, foscarnet, ganciclovir, idoxuridine, indinavir, inosine pranobex, lamivudine, nelfinavir, nevirapine, oseltamivir, palivizumab, penciclovir, pleconaril, ribavirin, rimantadine, ritonavir, ruprintrivir, saquinavir, stavudine, valaciclovir, zalcitabine, zanamivir, zidovudine and interferons; AIDS adjunct agents including dapsone; aminoglycosides including tobramycin; antifungals including amphotericin, caspofungin, clotrimazole, econazole nitrate, fluconazole, itraconazole, ketoconazole, miconazole, nystatin, terbinafine and voriconazole; anti-malarial agents including quinine; antituberculosis agents including capreomycin, ciprofloxacin, ethambutol, meropenem, piperacillin, rifampicin and vancomycin; beta-lactams including cefazolin, cefmetazole, cefoperazone, cefoxitin, cephacetrile, cephalexin, cephaloglycin and cephaloridine; cephalosporins, including cephalosporin C and cephalothin; cephamycins such as cephamycin A, cephamycin B, cephamycin C, cephapirin and cephradine; leprostatics such as clofazimine; penicillins including amoxicillin, ampicillin, amylpenicillin, azidocillin, benzylpenicillin, carbenicillin, carfecillin, carindacillin, clometocillin, cloxacillin, cyclacillin, dicloxacillin, diphenicillin, heptylpenicillin, hetacillin, metampicillin, methicillin, nafcillin, 2-pentenylpenicillin, penicillin N, penicillin O, penicillin S and penicillin V; quinolones including ciprofloxacin, clinafloxacin, difloxacin, grepafloxacin, norfloxacin, ofloxacine and temafloxacin; tetracyclines including doxycycline and oxytetracycline; miscellaneous anti-infectives including linezolide, trimethoprim and sulfamethoxazole; (21) anti-neoplastic agents such as, for example, droloxifene, tamoxifen and toremifene; (22) antiparkisonian drugs such as, for example, amantadine, andropinirole, apomorphine, baclofen, benserazide, biperiden, benztropine, bromocriptine, budipine, cabergoline, carbidopa, eliprodil, entacapone, eptastigmine, ergoline, galantamine, lazabemide, levodopa, lisuride, mazindol, memantine, mofegiline, orphenadrine, trihexyphenidyl, pergolide, piribedil, pramipexole, procyclidine, propentofylline, rasagiline, remacemide, ropinerole, selegiline, spheramine, terguride and tolcapone; (23) Antipsychotics such as, for example, acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine and zuclopenthixol; phenothiazines including aliphatic compounds, piperidines and piperazines; thioxanthenes, butyrophenones and substituted benzamides; (24) antirheumatic agents such as, for example, diclofenac, heparinoid, hydroxychloroquine and methotrexate, leflunomide and teriflunomide; (25) anxiolytics such as, for example, adinazolam, alpidem, alprazolam, alseroxlon, amphenidone, azacyclonol, bromazepam, bromisovalum, buspirone, captodiamine, capuride, carbcloral, carbromal, chloral betaine, chlordiazepoxide, clobenzepam, enciprazine, flesinoxan, flurazepam, hydroxyzine, ipsapiraone, lesopitron, loprazolam, lorazepam, loxapine, mecloqualone, medetomidine, methaqualone, methprylon, metomidate, midazolam, oxazepam, propanolol, tandospirone, trazadone, zolpidem and zopiclone; (26) appetite stimulants such as, for example, dronabinol; (27) appetite suppressants such as, for example, fenfluramine, phentermine and sibutramine; and anti-obesity treatments such as, for example, pancreatic lipase inhibitors, serotonin and norepinephrine re-uptake inhibitors, and anti-anorectic agents; (28) benzodiazepines such as, for example, alprazolam, bromazepam, brotizolam, chlordiazepoxide, clobazam, clonazepam, clorazepate, demoxepam, diazepam, estazolam, flunitrazepam, flurazepam, halazepam, ketazolam, loprazolam, lorazepam, lormetazepam, medazepam, midazolam, nitrazepam, nordazepam, oxazepam, prazepam, quazepam, temazepam and triazolam; (29) bisphosphonates such as, for example, alendronate sodium, sodium clodronate, etidronate disodium, ibandronic acid, pamidronate disodium, isedronate sodium, tiludronic acid and zoledronic acid; (30) blood modifiers such as, for example, cilostazol and dipyridamol, and blood factors; (31) cardiovascular agents such as, for example, acebutalol, adenosine, amiloride, amiodarone, atenolol, benazepril, bisoprolol, bumetanide, candesartan, captopril, clonidine, diltiazem, disopyramide, dofetilide, doxazosin, enalapril, esmolol, ethacrynic acid, flecanide, furosemide, gemfibrozil, ibutilide, irbesartan, labetolol, losartan, lovastatin, metolazone, metoprolol, mexiletine, nadolol, nifedipine, pindolol, prazosin, procainamide, propafenone, propranolol, quinapril, quinidine, ramipril, sotalol, spironolactone, telmisartan, tocamide, torsemide, triamterene, valsartan and verapamil; (32) calcium channel blockers such as, for example, amlodipine, bepridil, diltiazem, felodipine, flunarizine, gallopamil, isradipine, lacidipine, lercanidipine, nicardipine, nifedipine, nimodipine and verapamil; (33) central nervous system stimulants such as, for example, amphetamine, brucine, caffeine, dexfenfluramine, dextroamphetamine, ephedrine, fenfluramine, mazindol, methyphenidate, modafmil, pemoline, phentermine and sibutramine; (34) cholesterol-lowering drugs such as, for example, acipimox, atorvastatin, ciprofibrate, colestipol, colestyramine, bezafibrate, ezetimibe, fenofibrate, fluvastatin, gemfibrozil, ispaghula, nictotinic acid, omega-3 triglycerides, pravastatin, rosuvastatin and simvastatin; (35) drugs for cystic fibrosis management such as, for example, Pseudomonas aeruginosa infection vaccines (e.g., Aerugen™), α-1-antitripsin, amikacin, cefadroxil, denufosol, duramycin, glutathione, mannitol, and tobramycin; (36) diagnostic agents such as, for example, adenosine and aminohippuric acid; (37) dietary supplements such as, for example, melatonin and vitamins including vitamin E; (38) diuretics such as, for example, amiloride, bendroflumethiazide, bumetanide, chlortalidone, cyclopenthiazide, furosemide, indapamide, metolazone, spironolactone and torasemide; (39) dopamine agonists such as, for example, amantadine, apomorphine, bromocriptine, cabergoline, lisuride, pergolide, pramipexole and ropinerole; (40) drugs for treating erectile dysfunction, such as, for example, apomorphine, apomorphine diacetate, moxisylyte, phentolamine, phosphodiesterase type 5 inhibitors, such as sildenafil, tadalafil, vardenafil and yohimbine; (41) gastrointestinal agents such as, for example, atropine, hyoscyamine, famotidine, lansoprazole, loperamide, omeprazole and rebeprazole; (42) hormones and analogues such as, for example, cortisone, epinephrine, estradiol, insulin, Ostabolin-C, parathyroid hormone and testosterone; (43) hormonal drugs such as, for example, desmopressin, lanreotide, leuprolide, octreotide, pegvisomant, protirelin, salcotonin, somatropin, tetracosactide, thyroxine and vasopressin; (44) Hypoglycaemics such as, for example, sulphonylureas including glibenclamide, gliclazide, glimepiride, glipizide and gliquidone; biguanides including metformin; thiazolidinediones including pioglitazone, rosiglitazone, nateglinide, repaglinide and acarbose; (45) immunoglobulins; (46) Immunomodulators such as, for example, interferon (e.g., interferon beta-1a and interferon beta-1b) and glatiramer; (47) immunosupressives such as, for example, azathioprine, cyclosporin, mycophenolic acid, rapamycin, sirolimus and tacrolimus; (48) mast cell stabilizers such as, for example, cromoglycate, iodoxamide, nedocromil, ketotifen, tryptase inhibitors and pemirolast; (49) drugs for treatment of migraine headaches such as, for example, almotriptan, alperopride, amitriptyline, amoxapine, atenolol, clonidine, codeine, coproxamol, cyproheptadine, dextropropoxyphene, dihydroergotamine, diltiazem, doxepin, ergotamine, eletriptan, fluoxetine, frovatriptan, isometheptene, lidocaine, lisinopril, lisuride, loxapine, methysergide, metoclopramide, metoprolol, nadolol, naratriptan, nortriptyline, oxycodone, paroxetine, pizotifen, pizotyline, prochlorperazine propanolol, propoxyphene, protriptyline, rizatriptan, sertraline, sumatriptan, timolol, tolfenamic acid, tramadol, verapamil, zolmitriptan, and nonsteroidal anti-inflammatory drugs; (50) drugs for treatment of motion sickness such as, for example, diphenhydramine, promethazine and scopolamine; (51) mucolytic agents such as N-acetylcysteine, ambroxol, amiloride, dextrans, heparin, desulphated heparin, low molecular weight heparin and recombinant human DNase; (52) drugs for multiple sclerosis management such as, for example, bencyclane, methylprednisolone, mitoxantrone and prednisolone; (53) muscle relaxants such as, for example, baclofen, chlorzoxazone, cyclobenzaprine, methocarbamol, orphenadrine, quinine and tizanidine; (54) NMDA receptor antagonists such as, for example, mementine; (55) nonsteroidal anti-inflammatory agents such as, for example, aceclofenac, acetaminophen, alminoprofen, amfenac, aminopropylon, amixetrine, aspirin, benoxaprofen, bromfenac, bufexamac, carprofen, celecoxib, choline, cinchophen, cinmetacin, clometacin, clopriac, diclofenac, diclofenac sodium, diflunisal, ethenzamide, etodolac, etoricoxib, fenoprofen, flurbiprofen, ibuprofen, indomethacin, indoprofen, ketoprofen, ketorolac, loxoprofen, mazipredone, meclofenamate, mefenamic acid, meloxicam, nabumetone, naproxen, nimesulide, parecoxib, phenylbutazone, piroxicam, pirprofen, rofecoxib, salicylate, sulindac, tiaprofenic acid, tolfenamate, tolmetin and valdecoxib; (56) nucleic-acid medicines such as, for example, oligonucleotides, decoy nucleotides, antisense nucleotides and other gene-based medicine molecules; (57) opiates and opioids such as, for example, alfentanil, allylprodine, alphaprodine, anileridine, benzylmorphine, bezitramide, buprenorphine, butorphanol, carbiphene, cipramadol, clonitazene, codeine, codeine phosphate, dextromoramide, dextropropoxyphene, diamorphine, dihydrocodeine, dihydromorphine, diphenoxylate, dipipanone, fentanyl, hydromorphone, L-alpha acetyl methadol, levorphanol, lofentanil, loperamide, meperidine, meptazinol, methadone, metopon, morphine, nalbuphine, nalorphine, oxycodone, papaveretum, pentazocine, pethidine, phenazocine, pholcodeine, remifentanil, sufentanil, tramadol, and combinations thereof with an anti-emetic; (58) opthalmic preparations such as, for example, betaxolol and ketotifen; (59) osteoporosis preparations such as, for example, alendronate, estradiol, estropitate, raloxifene and risedronate; (60) other analgesics such as, for example, apazone, benzpiperylon, benzydamine, caffeine, cannabinoids, clonixin, ethoheptazine, flupirtine, nefopam, orphenadrine, pentazocine, propacetamol and propoxyphene; (61) other anti-inflammatory agents such as, for example, B-cell inhibitors, p38 MAP kinase inhibitors and TNF inhibitors; (62) phosphodiesterase inhibitors such as, for example, non-specific phosphodiesterase inhibitors including theophylline, theobromine, IBMX, pentoxifylline and papaverine; phosphodiesterase type 3 inhibitors including bipyridines such as milrinone, aminone and olprinone; imidazolones such as piroximone and enoximone; imidazolines such as imazodan and 5-methyl-imazodan; imidazoquinoxalines; and dihydropyridazinones such as indolidan and LY181512 (5-(6-oxo-1,4,5,6-tetrahydro-pyridazin-3-yl)-1,3-dihydro-indo1-2-one); dihydroquinolinone compounds such as cilostamide, cilostazol, and vesnarinone; motapizone; phosphodiesterase type 4 inhibitors such as cilomilast, etazolate, rolipram, oglemilast, roflumilast, ONO 6126, tolafentrine and zardaverine, and including quinazolinediones such as nitraquazone and nitraquazone analogs; xanthine derivatives such as denbufylline and arofylline; tetrahydropyrimidines such as atizoram; and oxime carbamates such as filaminast; and phosphodiesterase type 5 inhibitors including sildenafil, zaprinast, vardenafil, tadalafil, dipyridamole, and the compounds described in WO 01/19802, particularly (S)-2-(2-hydroxymethyl-1-pyrrolidinyl)-4-(3-chloro-4-methoxy-benzylamino)-5-[N-(2- yrimidinylmethyl)carbamoyl]pyrimidine, 2-(5,6,7,8-tetrahydro-1,7-naphthyridin-7-yl)-4-(3-chloro-4-methoxybenzylamino)-5-[N-(2-morpholinoethyl) carbamoyl]-pyrimidine, and (S)-2-(2-hydroxymethyl-l-pyrrolidinyl)-4-(3-chloro-4-methoxy-benzylamino)-5-[N-(1,3,5-trimethyl-4-pyrazolyl)carbamoyl]-pyrimidine); (63) potassium channel modulators such as, for example, cromakalim, diazoxide, glibenclamide, levcromakalim, minoxidil, nicorandil and pinacidil; (64) prostaglandins such as, for example, alprostadil, dinoprostone, epoprostanol and misoprostol; (65) respiratory agents and agents for the treatment of respiratory diseases including bronchodilators such as, for example, the .beta.2-agonists bambuterol, bitolterol, broxaterol, carmoterol, clenbuterol, fenoterol, formoterol, indacaterol, levalbuterol, metaproterenol, orciprenaline, picumeterol, pirbuterol, procaterol, reproterol, rimiterol, salbutamol, salmeterol, terbutaline and the like;

inducible nitric oxide synthase (iNOS) inhibitors; the antimuscarinics ipratropium, ipratropium bromide, oxitropium, tiotropium, glycopyrrolate and the like; the xanthines aminophylline, theophylline and the like; adenosine receptor antagonists, cytokines such as, for example, interleukins and interferons; cytokine antagonists and chemokine antagonists including cytokine synthesis inhibitors, endothelin receptor antagonists, elastase inhibitors, integrin inhibitors, leukotrine receptor antagonists, prostacyclin analogues, and ablukast, ephedrine, epinephrine, fenleuton, iloprost, iralukast, isoetharine, isoproterenol, montelukast, ontazolast, pranlukast, pseudoephedrine, sibenadet, tepoxalin, verlukast, zafirlukast and zileuton; (66) sedatives and hypnotics such as, for example, alprazolam, butalbital, chlordiazepoxide, diazepam, estazolam, flunitrazepam, flurazepam, lorazepam, midazolam, temazepam, triazolam, zaleplon, zolpidem, and zopiclone; (67) serotonin agonists such as, for example, 1-(4-bromo-2,5-dimethoxyphenyl)-2-aminopropane, buspirone, m-chlorophenylpiperazine, cisapride, ergot alkaloids, gepirone, 8-hydroxy-(2-N,N-dipropylamino)-tetraline, ipsaperone, lysergic acid diethylamide, 2-methyl serotonin, mezacopride, sumatriptan, tiaspirone, trazodone and zacopride; (68) serotonin antagonists such as, for example, amitryptiline, azatadine, chlorpromazine, clozapine, cyproheptadine, dexfenfluramine, R(+)-α-(2,3-dimethoxyphenyl)-1-[2-(4-fluorophenyl)ethyl]-4-piperidinemethanol, dolasetron, fenclonine, fenfluramine, granisetron, ketanserin, methysergide, metoclopramide, mianserin, ondansetron, risperidone, ritanserin, trimethobenzamide and tropisetron; (69) steroid drugs such as, for example, alcometasone, beclomethasone, beclomethasone dipropionate, betamethasone, budesonide, butixocort, ciclesonide, clobetasol, deflazacort, diflucortolone, desoxymethasone, dexamethasone, fludrocortisone, flunisolide, fluocinolone, fluometholone, fluticasone, fluticasone proprionate, hydrocortisone, methylprednisolone, mometasone, nandrolone decanoate, neomycin sulphate, prednisolone, rimexolone, rofleponide, triamcinolone and triamcinolone acetonide; (70) sympathomimetic drugs such as, for example, adrenaline, dexamfetamine, dipirefin, dobutamine, dopamine, dopexamine, isoprenaline, noradrenaline, phenylephrine, pseudoephedrine, tramazoline and xylometazoline; (71) nitrates such as, for example, glyceryl trinitrate, isosorbide dinitrate and isosorbide mononitrate; (72) skin and mucous membrane agents such as, for example, bergapten, isotretinoin and methoxsalen; (73) smoking cessation aids such as, for example, bupropion, nicotine and varenicline; (74) drugs for treatment of Tourette's syndrome such as, for example, pimozide; (75) drugs for treatment of urinary tract infections such as, for example, darifenicin, oxybutynin, propantheline bromide and tolteridine; (76) vaccines; (77) drugs for treating vertigo such as, for example, betahistine and meclizine; (78) therapeutic proteins and peptides such as acylated insulin, glucagon, glucagon-like peptides, exendins, insulin, insulin analogues, insulin aspart, insulin detemir, insulin glargine, insulin glulisine, insulin lispro, insulin zinc, isophane insulins, neutral, regular and insoluble insulins, and protamine zinc insulin; (79) anticancer agents such as, for example, anthracyclines, doxorubicin, idarubicin, epirubicin, methotrexate, taxanes, paclitaxel, docetaxel, cisplatin, vinca alkaloids, vincristine and 5-fluorouracil; (80) pharmaceutically acceptable salts or derivatives of any of the foregoing.

It should be noted that drugs listed above under a particular indication or class may also find utility in other indications. A plurality of active pharmaceutical ingredients can be employed in the practice of the present invention. The microcapsules of the present invention may also be used to deliver combinations of two or more different active pharmaceutical ingredients. Specifically active pharmaceutical ingredient delivery systems according to the invention may also be used to deliver combinations of three or more different active pharmaceutical ingredients. It will be clear to a person of skill in the art that, where appropriate, the active pharmaceutical ingredients may be linked to a carrier molecule or molecules and/or used in the form of prodrugs, salts, as esters, or as solvates to optimize the activity and/or stability of the active agent or drug.

The phrase "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

EXAMPLES

Materials.

Sudan Black is 2,2-dimethyl-1,3-dihydroperimidin-6-yl)-(4-phenylazo-1-naphthyl)diazene, with the formula of $C_{29}H_{24}N_6$. It is a nonfluorescent, thermostable lysochrome diazo dye used for staining of neutral triglycerides and lipids on frozen sections and some lipoproteins on paraffin sections. It has the appearance of a dark brown to black powder.

Tween 20 (Croda Americas, Wilmington, Del.) is a polyoxyethylene derivative of sorbitan monolaurate. The mean number of ethylene oxide groups is nominally 20 per molecule. This polysorbate surfactant commonly serves as a detergent or an emulsifier in a number of domestic, scientific, and pharmacological applications.

Triton X-100 is polyethylene glycol p-(1,1,3,3-tetramethylbutyl)-phenyl ether, comprising on average 9.5 ethylene oxide groups. It is used as a nonionic surfactant.

Example 1

A mixture comprising water (20 mL), ethyl acetate (5 mL), sodium hydrogen carbonate (0.580 g), about 1.0 mg of Sudan Black, and a drop of Tween 20 was mixed vigorously at room temperature using a mechanical stirrer (about 500 RPM) for 5 minutes. About 77 mg of 1,3-bischlorosulfonylbenzene was added to the mixture and stirred for about 3 minutes. The mixture was then treated with 3,5-diaminobenzoic acid, and vigorously stirred for additional 72 hours.

Example 2

The procedure of Example 1 was repeated, except that the mixture was treated with with 1,3-diaminobenzene instead of with 3,5-diaminobenzoic acid. The results were similar as in Example 1.

Example 3

A mixture of water (2.5 ml) and ethyl acetate (19 ml), Triton X-100 (2 drops), and 5-acetoxyresorcinol (92 mg) was mixed vigorously at room temperature. After about 3 minutes 1,2-bis(bromomethyl)-4-benzyloxybenzene (4-benzyloxy-1,2-xylylene dibromide) (282 mg) was added. After 20 minutes of additional stirring, an aliquot was sampled and examined under a microscope. The mean diameter of the formed capsules is about 10 microns. The stirring is continued for 24 hours. The mixture is filtered and the capsules are collected and washed. The observed mean diameter is about 2 to 5 microns.

To observe the reaction occurring in the mixture, aliquots are taken after 30 minutes from the beginning of the vigorous stirring and at 12 hour intervals thereafter. As observed on a microscope, the aliquots showed a formation of 1 to 2 micron capsules with the presence of the colorant Sudan black inside of them. The reaction is over probably after a few hours. It is postulated that the capsules have several —COOH groups on the surface.

Example 4

A mixture of heptane (45.0 mL), water (5.0 mL), Triton X 1000 (5 drops), bromocresol green (a trace amount), and 3,5-diaminobenzoic acid (152 mg, 1 mmol) were stirred vigorously for a few minutes. m-Phenylenediisocyanate (138 mg, 0.8 mmol) was added and the mixture was stirred for additional 6 hours. The mixture was filtered, and the solids were collected, washed and suspended in water. Microcapsules with green color inside of them were observed under a microscope. The mean capsule diameter was about 10 microns, with a narrow size distribution. The yield was about 35%.

Example 5

Tetraethylene glycol mono acetate was reacted with tosyl chloride in the presence of pyridine to produce a tosylate in quantitative yield. The tosylate was then reacted with cis-1,3-benzylideneglycerol in the presence of potassium carbonate and a phase transfer catalyst (Adogen 464 or Alliquat 336; about 1 mole %) to form a mixture comprising Product (I). Product (I) comprised acetyl groups which were hydrolyzed using 1.6% solution of ammonia in methanol to generate a benzylidene derivative (II) containing one primary hydroxyl group. Both Product (I) and the benzylidene derivative (II) were observed to be sufficiently hydrophilic to ensure the water solubility of the relevant diol during the interphase condensation polymerization.

Example 6

The benzylidene derivative (II) from Example 5 was reacted with propargyl bromide in the presence of potassium carbonate and Adogen 464 to yield alkyne product (III). The alkyne product (III) is envisioned to react with an azide to form a click reaction product.

Example 7

The benzylidene derivative (II) from Example 5 was reacted with acryloyl chloride in the presence of triethylamine to form acrylic acid ester (IV). The acrylic ester is envisioned to act as a thiol acceptor in a Michael addition in another click process.

Example 8

Product (I) from Example 5 was reacted with a dilute acid to remove the benzylidene groups. A corresponding diol (V) was thus obtained.

Example 9

Product (III) from Example 6 was reacted with a dilute acid to remove the benzylidene groups. A corresponding diol (VI) was thus obtained.

Example 10

Product (IV) from Example 7 was reacted with a dilute acid to remove the benzylidene groups. The corresponding diol (VII) was thus obtained.

Example 11

4-hydroxyphthalic acid (1 molar equivalent) was dissolved in acetonitrile and reacted with sodium hydroxide (3 molar equivalents), followed by an addition of benzyl bromide (1.02 molar equivalents) to form a reaction mixture containing benzyloxy derivative (VIII). The reaction mixture was neutralized with Dowex resin. The reaction mixture was then treated with pyridine and thionyl chloride (2.5 molar equivalents, introduced dropwise). The reaction mixture was worked up followed by a vacuum distillation to produce water-insoluble 4-benzyloxypthaloyl chloride (IX).

Example 12

A mixture of 0.30 mmol diol (V), 0.30 mmol of diol (VI), 0.30 mmol of diol (VII), 0.10 mmol glycerol, 1.0 mmol of 1,3-propanediol and 240 mg of active pharmaceutical ingredient allopurinol were dissolved in 2.5 mL of water to create a mixture. A surfactant (Triton X 100; 5 drops), and a solution of methyl isobutyl ketone (MIBK) containing pyridine (3 mmoles) and bifunctional acid chloride (IX, 2.0 moles) were added to the mixture. The mixture was stirred vigorously (at 1000 RPM) at room temperature. Aliquots are sampled every hour and examined under the microscope to determine that no additional change to the mixture was observed. After a period of five hours, the mixture was filtered, and the formed microcapsules were isolated and washed several times with water and ethyl acetate and dried. No allopurinol could be detected in the filtrate or the washings. The average diameter of the resulting capsules was about 750 nm.

The capsules contained the following groups on the surface: (a) an acetyl group, which can be removed by hydrolysis and replaced with other functionality; (b) a benzyl group, which can be removed by hydrogenation and replaced, (c) a propargyl group, which can be reacted with the azide functionality; and (d) an acrylic group which can be reacted with thiol functionality.

Example 13

Oil soluble 1,3-bischlorosulfonylbenzene (275 mg, 1.0 mmoles) was dissolved in ethyl acetate (2.0 mL) to create a mixture. Oil soluble steroid estradiol (100 mg, 0.368 mmoles) was added to the mixture, followed by an addition of an aqueous solution of diol V (0.15 mmole), diol VI (0.15 mmole), diol VII (0.15 mmole), glycerol (0.10 mmole), 1,3-propanediol (0.45 mmole) and Tween 20 (4 drops) dissolved in water (21.0 mL). The mixture is vigorously stirred (1000 RPM) for 4 hours. The formed microcapsules were filtered off, washed several times with water and ethyl acetate, and dried. No estradiol was detected outside of microcapsules. The surface of the microcapsules contained acetyl, propargyl and acrylic functional groups.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

What is claimed is:

1. A microcapsule comprising a core encapsulated by a polymeric shell, wherein
the core comprises an active pharmaceutical ingredient;
the polymeric shell comprises polymeric material selected from the group consisting of polyether, polyester, polyamine, polyamide, polyurea, polyurethane, polythiocarbamate, polythiocarbonate, and polytriazole;
the shell comprises an inner surface and an outer surface, wherein the outer surface comprises a surface functional group selected from the group consisting of—OH, —COOH, —NH$_2$, —NHR", and a mixture of the foregoing, wherein R" is a C$_1$ to C$_7$ hydrocarbon group, wherein at least some of the surface function groups are protected by a protecting group;
wherein the microcapsule is a controlled release microcapsule.

2. The microcapsule of claim 1, wherein the polymeric shell is formed by a reaction of at least one water-soluble monomer comprising at least two polymerization functional hydroxyl groups; and at least one oil-soluble monomer, comprising at least two polymerization functional groups selected from the group consisting of a halide, acyl halide, sulfonyl halide, isocyanate, and isothiocyanate.

3. The microcapsule of claim 1, wherein the polymeric shell is formed by a reaction of at least one water-soluble monomer comprising at least two polymerization functional primary amine groups; and
at least one oil-soluble monomer comprising at least two polymerization functional groups selected from the group consisting of a halide, acyl halide, sulfonyl halide, isocyanate, and isothiocyanate.

4. The microcapsule of the claim 1 wherein the polymeric shell is formed by a reaction of at least one water-soluble monomer comprising either at least two hydroxyl polymerization functional groups or at least two primary amine polymerization functional groups; and
at least one oil-soluble monomer comprising at least two acyl halide polymerization functional groups.

5. The microcapsule of claim 1 wherein the polymeric shell is formed by a reaction of at least one water-soluble monomer comprising at least two polymerization functional groups selected from the group consisting of primary amine groups and hydroxyl groups; and
at least one oil-soluble monomer comprising at least two sulfonyl halide polymerization functional groups, or at least two isocyanate polymerization functional groups, or at least two isothiocyanate polymerization functional groups.

6. The microcapsule of claim 1 wherein the polymeric shell is formed by a reaction of at least one water-soluble monomer comprising at least two alkyne polymerization functional groups; and
at least one oil-soluble monomer comprising at least two azide polymerization functional groups.

7. The microcapsule of claim 1, wherein the polymeric shell is formed by a reaction of at least oil-soluble monomer comprising at least two polymerization functional groups selected from the group consisting of hydroxyl, phenoxyl, carboxylic acid, primary amine, secondary amine, sulfonic acid, and alkyne; and
at least one water-soluble monomer, comprising at least two polymerization functional groups selected from the group consisting of a halide, acyl halide, isocyanate, thiol, and azide;
wherein the water-soluble monomer or the oil-soluble monomer or both, further comprises at least one surface functional group.

8. The microcapsule of claim 7, wherein the polymeric shell is formed by a reaction of at least one oil-soluble monomer comprising at least two hydroxyl polymerization functional groups; and at least one water-soluble monomer, comprising at least two polymerization functional groups selected from the group consisting of a halide, acyl halide, and isocyanate.

9. The microcapsule of claim 7, wherein the polymeric shell is formed by a reaction of at least one oil-soluble monomer comprising at least two primary amine polymerization functional groups; and
at least one water-soluble monomer comprising at least two polymerization functional groups selected from the group consisting of a halide, acyl halide, and isocyanate.

10. The microcapsule of claim 7, wherein the polymeric shell is formed by a reaction of at least one oil-soluble diacid salt; and at least one water-soluble dihalide.

11. The microcapsule of claim 7 wherein the polymeric shell is formed by a reaction of at least one oil-soluble monomer comprising at least two hydroxyl polymerization functional groups or at least two primary amine polymerization functional groups; and
at least one water-soluble monomer comprising at least two acyl halide polymerization functional groups.

12. The microcapsule of claim 7 wherein the polymeric shell is formed by a reaction of at least one oil-soluble monomer comprising at least two polymerization functional groups selected from the group consisting of primary amine groups and hydroxyl groups; and
at least one water-soluble monomer comprising at least two sulfonyl halide polymerization functional groups, or at least two isocyanate polymerization functional groups.

13. The microcapsule of claim 7 wherein the polymeric shell is formed by a reaction of at least one oil-soluble monomer comprising at least two polymerization functional alkyne groups; and
  at least one water-soluble monomer comprising at least two azide polymerization functional groups.

14. The microcapsule of claim 1, wherein the polymeric shell is formed by a reaction of
  at least one water-soluble monomer comprising at least two polymerization functional groups selected from the group consisting of hydroxyl, phenoxyl, carboxylic acid, primary amine, secondary amine, sulfonic acid, alkene, and alkyne; and
  at least one oil-soluble monomer, comprising at least two polymerization functional groups selected from the group consisting of a halide, acyl halide, sulfonyl halide, isocyanate, isothiocyanate, thiol, and azide;
  wherein the water-soluble monomer or the oil-soluble monomer or both, further comprises at least one surface functional group protected by a protecting group.

15. The microcapsule of claim 1, wherein the protecting group is selected from the group consisting of acetyl, Ac, benzoyl, Bz, benzyl, Bn, β-methoxyethoxymethyl ether, MEM, methoxytrityl, (4-methoxyphenyl)diphenylmethyl, MMT, dimethoxytrityl, bis-(4-methoxyphenyl)phenylmethyl, DMT, methoxymethyl ether, MOM, p-methoxybenzyl ether, PMB, methylthiomethyl ether, pivaloyl, Piv, tetrahydropyranyl, THP, tetrahydrofuryl, THF, trityl, triphenylmethyl, Tr, silyl ether, trimethylsilyl, TMS, tert-butyldimethylsilyl, TBDMS, tri-iso-propylsilyloxymethyl, TOM, triisopropylsilyl, TIPS, methyl ether, ethoxyethyl ether, carbobenzyloxy, Cbz, p-methoxybenzyl carbonyl, Moz, MeOZ, tert-butyloxycarbonyl, BOC, 9-fluorenylmethyloxycarbonyl, FMOC, carbamate, p-methoxybenzyl, 3,4-Dimethoxybenzyl, DMPM, p-methoxyphenyl, PMP, tosyl, Ts, nosyl, methyl ester, benzyl ester, tert-butyl ester, 2,6-disubstituted phenol ester, 2,6-dimethyl phenol, 2,6-diisopropylphenol, 2,6-di-tert-butylphenol, silyl esters, orthoesters, and oxazoline.

16. The microcapsule of claim 1, wherein the surface functional group is a pendant group that does not react in a condensation polymerization to form the microcapsule.

17. The microcapsule of claim 1, wherein the controlled release microcapsule is suitable to release the active pharmaceutical ingredient from the microcapsule by a pH change, a presence of enzymes, ultrasound, or ferromagnets.

18. The microcapsule of claim 1, wherein the diameter of the microcapsule is between 50 nanometers and 10 micrometers.

19. A medical composition for use in administration to a patient comprising the microcapsule of claim 1.

20. The medical composition of claim 19, wherein the medical composition is administered orally, intravenously, rectally, sublingually, or subcutaneously.

* * * * *